(12) United States Patent
Uejima

(10) Patent No.: US 7,079,229 B2
(45) Date of Patent: Jul. 18, 2006

(54) DENSITOMETRY DEVICE

(75) Inventor: Atsushi Uejima, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 237 days.

(21) Appl. No.: 10/253,891

(22) Filed: Sep. 25, 2002

(65) Prior Publication Data

US 2003/0072002 A1    Apr. 17, 2003

(30) Foreign Application Priority Data

Sep. 28, 2001 (JP) .............................. 2001-304127

(51) Int. Cl.
*G06K 9/74* (2006.01)

(52) U.S. Cl. ...................... 356/61; 356/445; 347/241; 347/238

(58) Field of Classification Search ................ 356/71, 356/73, 429, 445, 446, 448; 347/241, 256, 347/238

See application file for complete search history.

(56) References Cited

U.S. PATENT DOCUMENTS

| | | | | |
|---|---|---|---|---|
| 6,172,745 B1 * | 1/2001 | Voser et al. | .................. | 356/71 |
| 6,473,165 B1 * | 10/2002 | Coombs et al. | ............... | 356/71 |
| 6,480,219 B1 * | 11/2002 | Uejima et al. | .............. | 347/241 |
| 6,512,577 B1 * | 1/2003 | Ozanich | ...................... | 356/73 |

* cited by examiner

*Primary Examiner*—Layla G. Lauchman
(74) *Attorney, Agent, or Firm*—Sughrue Mion, PLLC

(57) ABSTRACT

The present invention relates to a densitometry device that can perform suitable densitometry with minimum required light amounts and can achieve space savings. An angle θ between a reference optical axis of a light source, which is an LED chip, and an optical axis, according to a photoelectric conversion element, of a density measurement optical system is set to, for example, 52°. Light-emitting chips, which emit each of red, green and blue light, are provided inside a cannon shell-shaped light-emitting portion. These light-emitting chips are arranged in a straight line along a direction of conveyance of a color patch chart. Consequently, inclination angles of the light-emitting chips with respect to a measurement axis of the density measurement optical system will always change consistently with each other, and no difference between the inclination angles of the different colors will occur.

12 Claims, 17 Drawing Sheets

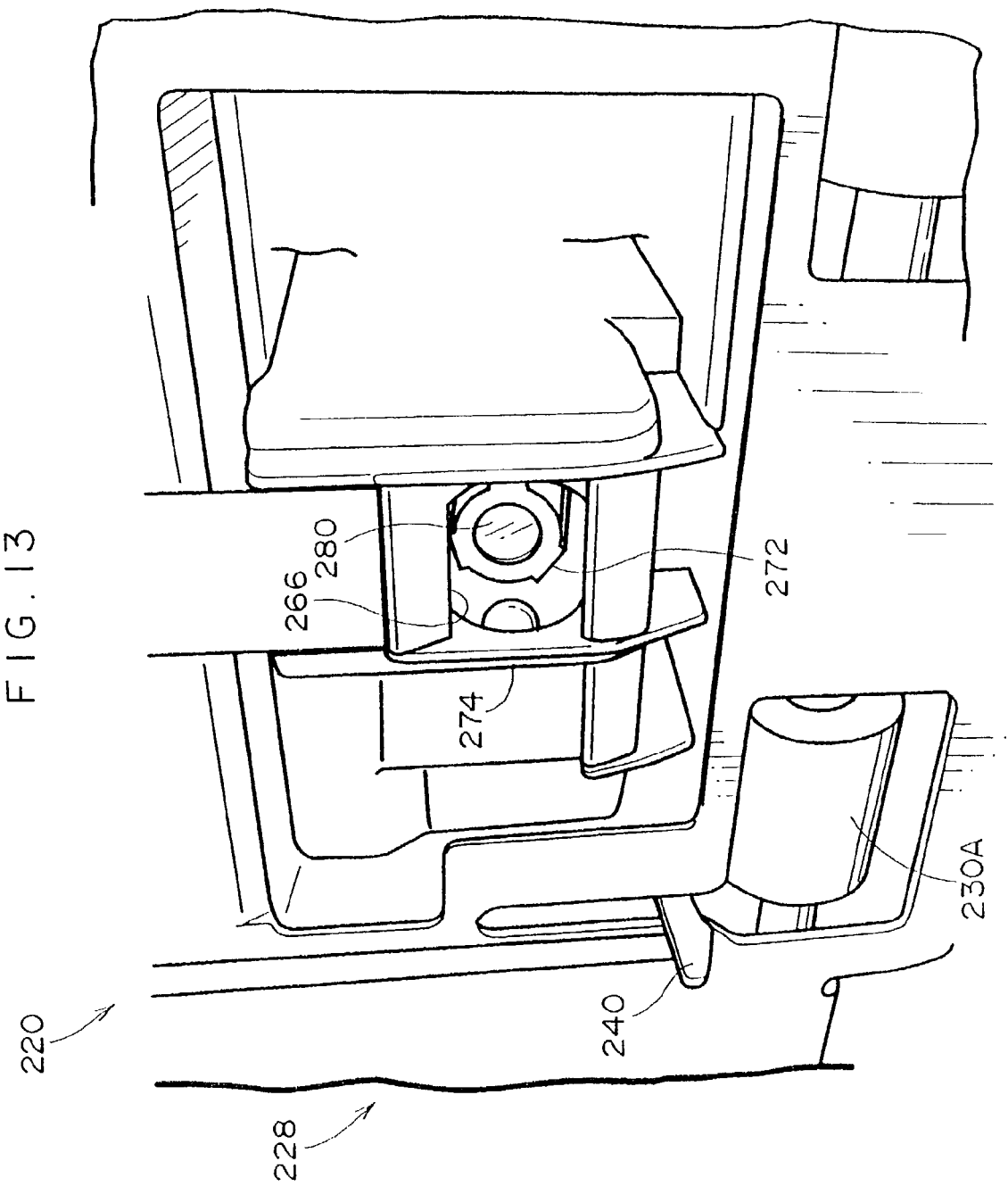

DIRECTION OF ARRANGEMENT

DIRECTION OF ARRANGEMENT

DENSITOMETRY DEVICE

BACKGROUND OF THE INVENTION

1. Field of the Invention

The present invention relates to a densitometry device provided with a density measurement optical system for sequentially reading densities of respective density patterns, using LEDs as light sources, for an object of measurement on which an image is recorded.

2. Description of the Related Art

Conventionally, in an image-recording device that records images, compensation is required for color reproduction during image recording. Therefore, when paper used for recording is exchanged (including times when a magazine is exchanged but the type of paper is unchanged), recording of an image based on previously stored pattern data is performed, and recording paper that is output with the results thereof is used as a color patch chart. The pattern data includes a number of gradations of different densities (brightnesses) for each color. A densitometry device is provided at the image-recording device. The densitometry device measures the densities of the patches of each color, which have been recorded with the number of different gradations. During this measurement, the surface of the color patch chart is illuminated with light from a light source such as a halogen lamp, and density measurements are carried out with sequential switching between R, G and B filters. Thus, accurate density values can be obtained.

Density values of the standard pattern data are compared with the measured values. When there is found to be a difference, compensation data is created to compensate for the difference, and this compensation data is entered into a memory or the like at the image-recording device.

Thereafter, when usual image recording is to be carried out, image data that is input is subjected to compensation with the compensation data. Consequently, color reproducibility with respect to image data is always suitably maintained, and reductions of image quality due to color reproduction failures and the like can be prevented.

However, because the halogen lamps and the like that are used as light sources in the aforementioned densitometry devices emit light that is nearly white, a plurality of photoelectric conversion elements must be provided, and optical filters for color separation are required. Furthermore, even if LEDs, which emit monochromatic light, are used, each LED must be packaged separately. Thus, the number of components increases, and the image-recording device becomes larger.

SUMMARY OF THE INVENTION

An object of the present invention is to provide a densitometry device that can achieve a saving of space.

Another object of the present invention is to provide a densitometry device that can greatly reduce directly reflected and/or transmitted light, which have a remarkably deleterious effect on the accuracy of densitometry values, and that can thus raise accuracy for high densities.

According to a first aspect of the present invention, a densitometry device for measuring densities of an object of measurement on which a color image is formed that includes a pattern of different densities for each of colors is provided, the device including: an LED light source that includes an individual package and a plurality of light-emitting chips enclosed in the package for illuminating light of at least two colors onto the object of measurement; and a density measurement optical system that photoelectrically converts light that has been at least one of reflected from and transmitted through the object of measurement for obtaining electric signals, such that densities of each of the density patterns can be obtained from the electric signals.

In this aspect, because the light source is an LED light source, a minimum required light amount can be obtained. Moreover, because the light-emitting chip for emitting the light is enclosed in a single resin package, light sources for a plurality of colors can be provided in the space of a single light source, and a reduction of space requirements can be achieved.

According to a second aspect of the present invention, a densitometry device is provided, the device including: a light source for illuminating an object of measurement on which an image is formed that includes a pattern of different densities; and a density measurement optical system that photoelectrically converts light that has been at least one of reflected from and transmitted through the object of measurement, for obtaining densities of the pattern of densities. An optical axis of the light source and an optical axis of the density measurement optical system are set such that, during illumination of the object of measurement, the optical axes form an angle in the range from 47° to 55°.

This angle, θ, is set in a range such that a light amount required for measuring density is assuredly provided when the light source (that is, the LED light source) is caused to illuminate by a certain voltage, and such that light from the light source that has been reflected or transmitted at the surface of the object of measurement (for example, a chart sheet) is not directly incident on a reading element of the density measuring system. This allowable range is 47° to 55°. That is, if the angle of irradiation is less than 47°, the amount of light energy per unit area of the object of measurement will be large, and reflected light amounts and transmitted light amounts will be large. Consequently, when measurements of densities of the object of measurement are performed, light reflected or transmitted due to errors in the angle of irradiation will be directly incident on the reading element, and reading errors will tend to occur for a high density range. On the other hand, if the angle of irradiation is more than 55°, the amount of light energy per unit area of the object of measurement will be small, and light amounts appropriate for density measurement can not be obtained.

More specifically, the pattern of densities of the object of measurement includes an arrangement direction, and the light source includes a plurality of light-emitting chips arranged along a single straight row, a direction of arrangement of the light-emitting chips substantially coinciding with the arrangement direction of the density pattern.

Consequently, even if each light-emitting chip is inclined with respect to a predetermined position, every light-emitting chip will be inclined uniformly and there will be no angular difference between the light-emitting chips. Moreover, by providing a plurality of the light-emitting chips for the same color, the amount of light emitted onto the object of measurement can be increased.

Preferably, each of the light-emitting chips is capable of emitting light of a color, and the colors that can be emitted by the light-emitting chips are different from one another.

By arranging light-emitting chips that emit mutually different colors, density measurement can be applied to an object of measurement on which a color image has been formed.

Also preferably, the densitometry device further includes a plurality of power supply terminals for enabling the light-emitting chips to emit light, each of the terminals including a distal end portion for connecting to a corresponding lead and being shielded by an insulating member, and a proximal end portion which is bent such that positions to be shielded are maintained substantially in a state of non-contact with respect to one another.

A pitch dimension of the power supply terminals that is suitable for inserting the power supply terminals, which cause the light-emitting chips to emit light, through a base plate before soldering the terminals may be unsuitable for connecting direct leads. Therefore, portions at a side of the power supply terminals at which the leads are connected, that is, at a connection side (the distal end), are slanted, and can be covered with insulating members for preventing short-circuits between the terminals. Here, if base plate side end portions of the power supply terminals are bent, stress will be applied to these power supply terminals. In the present invention, because the power supply terminals are slanted from partway along the connection side, stress is alleviated.

Preferably, the terminals are arranged along an arrangement direction, and directions in which the terminals are bent coincide with the arrangement direction of the terminals.

For example, the power supply terminals may be inclined in mutually opposite directions. However, in consideration of work required for connecting the leads, it is desirable that the terminals be inclined along the same direction.

Also preferably, the densitometry device further includes a holding member with a pre-specified angle of inclination, and a gripping member through which the power supply terminals of the light source pass, the holding member and the gripping member resiliently supporting the light source, and the gripping member including a cutaway portion for avoiding contact thereof with the power supply terminals of the light source.

In order to maintain the light source (that is, the LED light source) at this predetermined angle of inclination θ, the preparatory holding member may be attached in advance. The holding member may be formed integrally with or previously assembled to, for example, a housing that holds the density measurement optical system. Thus, when the light source is attached, it can be held at the angle θ with certainty. Moreover, if the light source is sandwiched between the holding member and the gripping member by a resilient force of the gripping member, the assembly process is simple. In such a case, the gripping member may be provided with cutaway portions so as to not obstruct the power supply terminals. Thus, the light source can be assuredly pressed by the resilient force.

Also preferably, the densitometry device further includes a housing for holding the light source and the density measurement optical system, the housing being formed with electrically conductive members.

As a result, the effects of electrical noise on electronic components that are vulnerable to noise, such as, for example, density measuring elements in the density measurement optical system, can be alleviated.

BRIEF DESCRIPTION OF THE DRAWINGS

FIG. 13 is a perspective view of a barrel of a density measurement unit as viewed from a base portion side.

DESCRIPTION OF THE PREFERRED EMBODIMENTS

An embodiment of the present invention will be described for a case in which the invention is applied to an exposure device that uses a photosensitive material.

Figure 1:
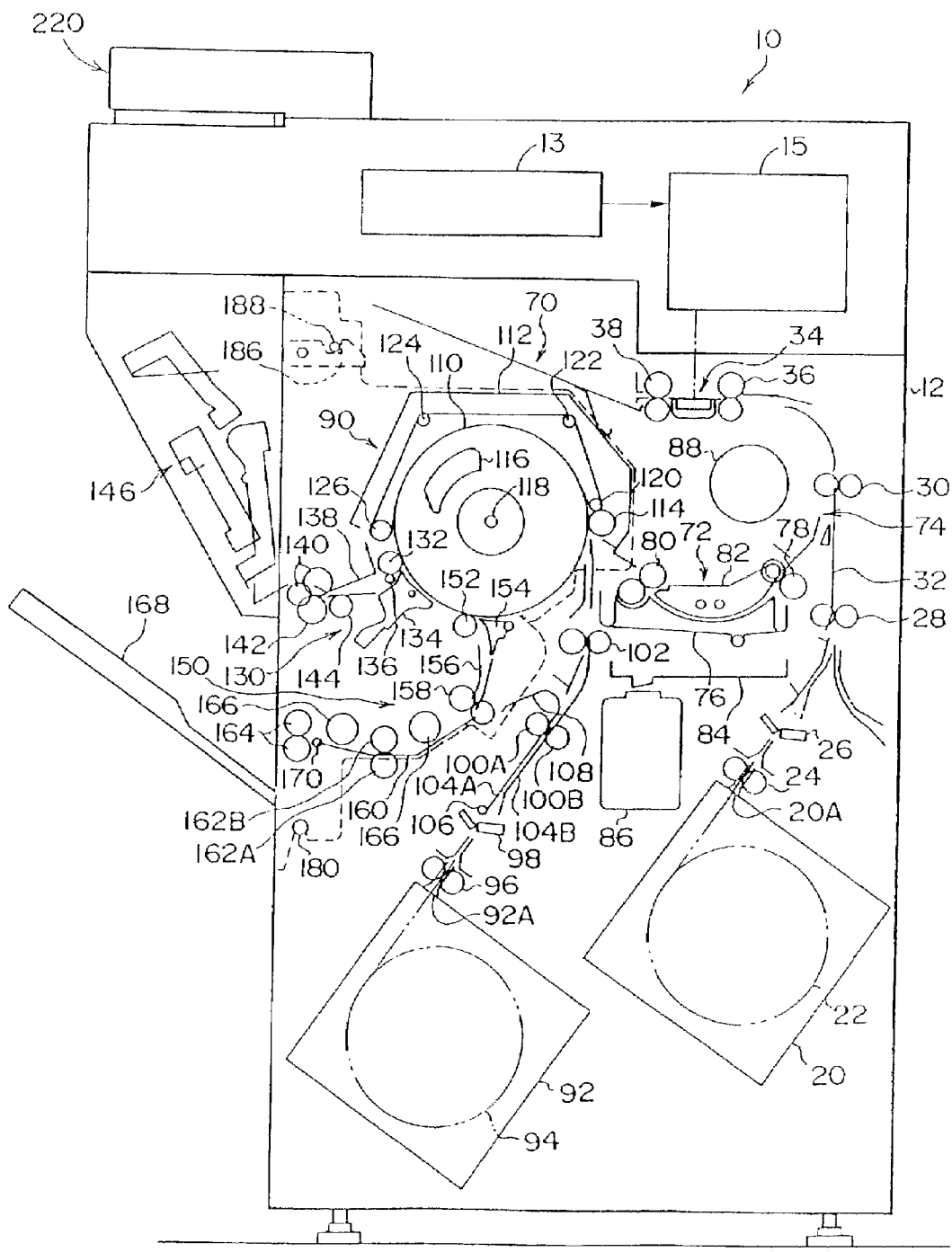
FIG. 1 is a schematic structural view of an image-recording device relating to an embodiment of the present invention.
Figure 2:
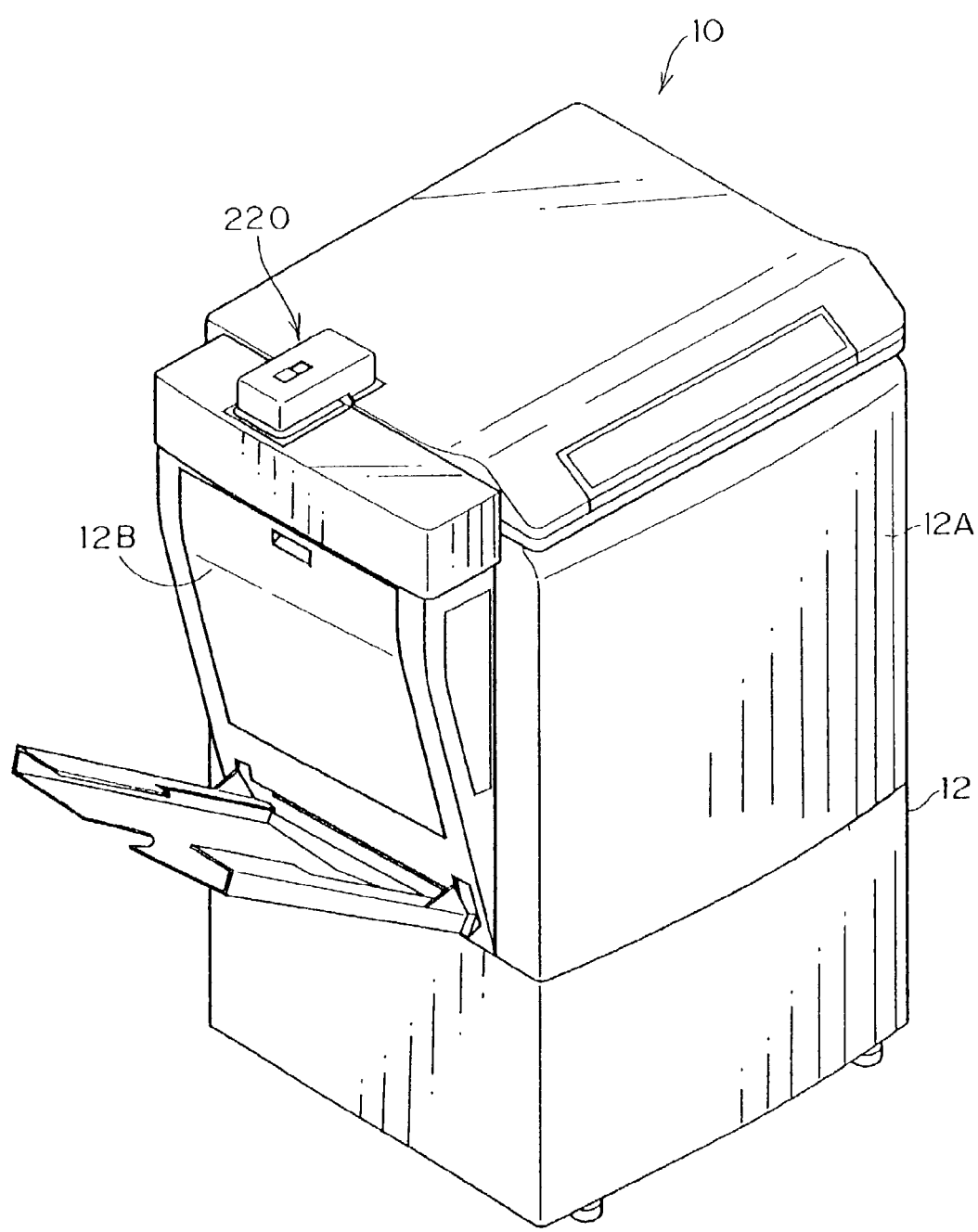
FIG. 2 is a perspective view showing an exterior of the image-recording device relating to the present embodiment.

FIG. 1 shows overall schematic structure of an image-recording device 10 relating to the present invention. FIG. 2 shows an oblique view of the exterior of the image-recording device 10. The illustrated image-recording device 10 forms an image by exposing an image onto a heat-developable photosensitive material, heat developing the same, and transferring the image to an image-receiving material.

The image-recording device 10 has an overall box-like structure. A front door 12A, a side door 12B and the like are installed on a machine stand 12. The interior of the machine stand 12 can be exposed by opening these doors.

An image-processing section 13 and an image-recording section 15 are provided at an upper portion of the machine stand 12 of the image-recording device 10. The image-processing section 13 receives image signals from an external portion, converts the signals to a file format appropriate for the image-recording device 10, and adjusts image size, colors, density and the like.

A photosensitive material magazine 20 is disposed inside the machine stand 12 of the image-recording device 10. A photosensitive material 22, which is wound up in a roll, is stored in the photosensitive material magazine 20. When the photosensitive material 22 is drawn out, a photosensitive surface thereof (exposure surface) faces in a direction downward and to the right of FIG. 1.

Nip rollers 24, which serve as drawing out rollers, are provided near a photosensitive material drawing out opening 20A of the photosensitive material magazine 20. When rotated, the nip rollers 24 draw out and convey the photosensitive material 22 from the photosensitive material magazine 20. A speed at which the photosensitive material 22 is conveyed by the nip rollers 24 may be, for example, 50 mm/sec.

A cutter 26 is disposed upward of the nip rollers 24. The cutter 26 cuts a predetermined length of the photosensitive material 22 that has been drawn out from the photosensitive material magazine 20 by the nip rollers 24. After operation of the cutter, the nip rollers 24 are rotated in reverse, and the photosensitive material 22 is rewound until just a little of a distal end portion of the material is nipped by the nip rollers 24.

Conveyance rollers 28, conveyance rollers 30 and a guide plate 32 are disposed upward of the cutter 26. These can convey the photosensitive material 22 that has been cut to the predetermined length to an exposure section 34.

The exposure section 34 is disposed between conveyance rollers 36 and conveyance rollers 38. When the photosensitive material 22 passes through the exposure section (an exposure position) between these rollers, the photosensitive material 22 is scanned (main-scanned) in a direction orthogonal to the conveyance direction by a light beam according to the image-processing section 13.

A switchback 70 is provided sideward (in FIG. 1) of the exposure section 34. Also, a water-coating section 72 is provided downward of the exposure section 34. The photosensitive material 22, which has been conveyed upward from the photosensitive material magazine 20 and scanned and exposed at the exposure section 34, is temporarily sent into the switchback 70. Then, by reverse rotation of the conveyance rollers 38, the conveyance rollers 36 and the conveyance rollers 30, the photosensitive material 22 is again passed through the exposure section 34, and fed into the water-coating section 72 via a junction portion 74, which is provided beneath the conveyance rollers 30.

A coating tank 76 is disposed at the water-coating section 72. The coating tank 76 is formed in a bowl-like shape, and an interior thereof is filled with water (a solvent for image formation). Feed rollers 78 are disposed at an upstream end portion with respect to a conveyance path of the photosensitive material 22 in the coating tank 76. In addition, a pair of squeeze rollers 80 are disposed at a downstream end portion with respect to the conveyance path of the photosensitive material 22 in the coating tank 76.

A guide plate 82, which faces the coating tank 76, is attached above the coating tank 76. The photosensitive material 22 is fed in between the guide plate 82 and the coating tank 76 and coated with water. Then, the squeeze rollers 80 grippingly convey the photosensitive material 22, thus removing excess water.

A ceramic heater is installed at an upper portion of the guide plate 82. The water can be heated (for example, to 40° C.±3° C.) and charged into the water tank 76.

A heat development and image transfer section 90 is disposed sideward (in FIG. 1) of the water-coating section 72. After passing through the squeeze rollers 80, the photosensitive material 22 is fed into heat development and image transfer section 90.

An image-receiving material magazine 92 is also disposed inside the machine stand 12, sideward (in FIG. 1) of the photosensitive material magazine 20. An image-receiving material 94, which is wound up in a roll, is stored in the image-receiving material magazine 92. A widthwise dimension of the image-receiving material 94 (for example, 127 mm) is smaller than a widthwise dimension of the photosensitive material 22. When the image-receiving material 94 is drawn out, an image-forming surface thereof faces downward and to the right of FIG. 1.

Nip rollers 96 are disposed near an image-receiving material drawing out opening 92A of the image-receiving material magazine 92. The nip rollers 96 can nip the image-receiving material 94 and draw it out from the image-receiving material magazine 92, and are capable of releasing nipping.

A cutter 98 is disposed upward of the nip rollers 96. In a similar manner to the cutter 26, the cutter 98 cuts the image-receiving material 94 that has been drawn out from the image-receiving material magazine 92, to a length shorter than the length to which the photosensitive material 22 is cut.

Conveyance rollers 100, conveyance rollers 102 and guide plates 104A and 104B are disposed upward of the cutter 98, at a position sideward of the photosensitive material magazine 20. These can convey the image-receiving material 94 that has been cut to a predetermined length to the heat development and image transfer section 90.

At the heat development and image transfer section 90, a heating drum 110, around which the photosensitive material 22 and the image-receiving material 94 are fed, is provided. A curve guide roller 132 is disposed adjacent to the heating drum 110 and a separation pawl 134 is rotatably supported substantially below the heating drum 110, at a material feed direction downstream side of the curve guide roller 132. A pinch roller 136 is also disposed thereat.

The separation pawl 134 faces an outer periphery of the heating drum 110, and can be contacted with and moved apart from the heating drum 110 by operation of a cam 116. The photosensitive material 22 and the image-receiving material 94 are superposed and grippingly conveyed between the heating drum 110 and an endless pressure belt 112. A distal end portion of the photosensitive material 22 projects distally further than the image-receiving material 94 by a predetermined length. When the separation pawl 134 abuts against the heating drum 110, of the materials, only this distal end portion of the photosensitive material 22 engages with the separation pawl 134. Thus, this distal end portion can be peeled from the outer periphery of the heating drum 110. The pinch roller 136 operates in concert with the separation pawl 134. When the separation pawl 134 is apart from the heating drum 110, the pinch roller presses against the curve guide roller with a predetermined pressure (for example, 600 g). As a result, the photosensitive material 22 that has been peeled off by the separation pawl 134 is pressed by the pinch roller 136 while being wound round the curve guide roller 132. By this structure, the photosensitive material 22 is moved sideward (in FIG. 1).

A guide plate 138 is disposed sideward in FIG. 1 of the curve guide roller 132 and the separation pawl 134. Further, photosensitive material discharge rollers 140, a backup roller 142 and a guide roller 144 are disposed at a distal end portion of the guide plate 138. The photosensitive material discharge rollers 140 are of a type known as "corrugation rollers", and mesh with each other. The backup roller 142 contacts with one of the photosensitive material discharge rollers 140. Accordingly, the photosensitive material 22 that has been wound round the curve guide roller 132 and moved sideward can be further conveyed and accumulated in a waste photosensitive material storage bin 146. The rotation speed of the photosensitive material discharge rollers 140 is set to be 1 to 3% faster than the speed of the heating drum 110. Thus, slackening of the photosensitive material 22 and adherence thereof to the guide plate 138 are prevented.

A second separation and conveyance section 150 is disposed at a side of the separation pawl and beneath the heating drum 110. A separation roller 152 and a separation pawl 154 are disposed at the second separation and conveyance section 150 beneath the heating drum 110. The separation roller 152 is a rubber roller made of silicone rubber, and a surface roughness thereof is not more than 12.5 S. Driving force from a driving motor is transmitted to the separation roller 152 and rotates the same. The separation roller 152 presses against the outer periphery of the heating drum 110 with a predetermined pressure (for example, 400 g). Thus, the separation roller 152 can move with the heating drum 110 and operate together with the separation pawl 154 to peel off the image-receiving material 94 from the outer periphery of the heating drum 110 and curvingly guide the material.

A guide plate 156 and image-receiving material discharge rollers 158 are disposed downward of the separation roller 152 and the separation pawl 154. The guide plate 156 and image-receiving material discharge rollers 158 guide and convey the image-receiving material 94 that has been peeled off the heating drum by the separation roller 152 and the separation pawl 154. Further, an image-receiving material guide 160, image-receiving material discharge rollers 162, image-receiving material discharge rollers 164 and guide rollers 166 are disposed sideward of the image-receiving material discharge rollers 158. Thus, the image-receiving material that has been conveyed by the image-receiving material discharge rollers 158 can be conveyed further and discharged to a tray 168.

Figure 3:
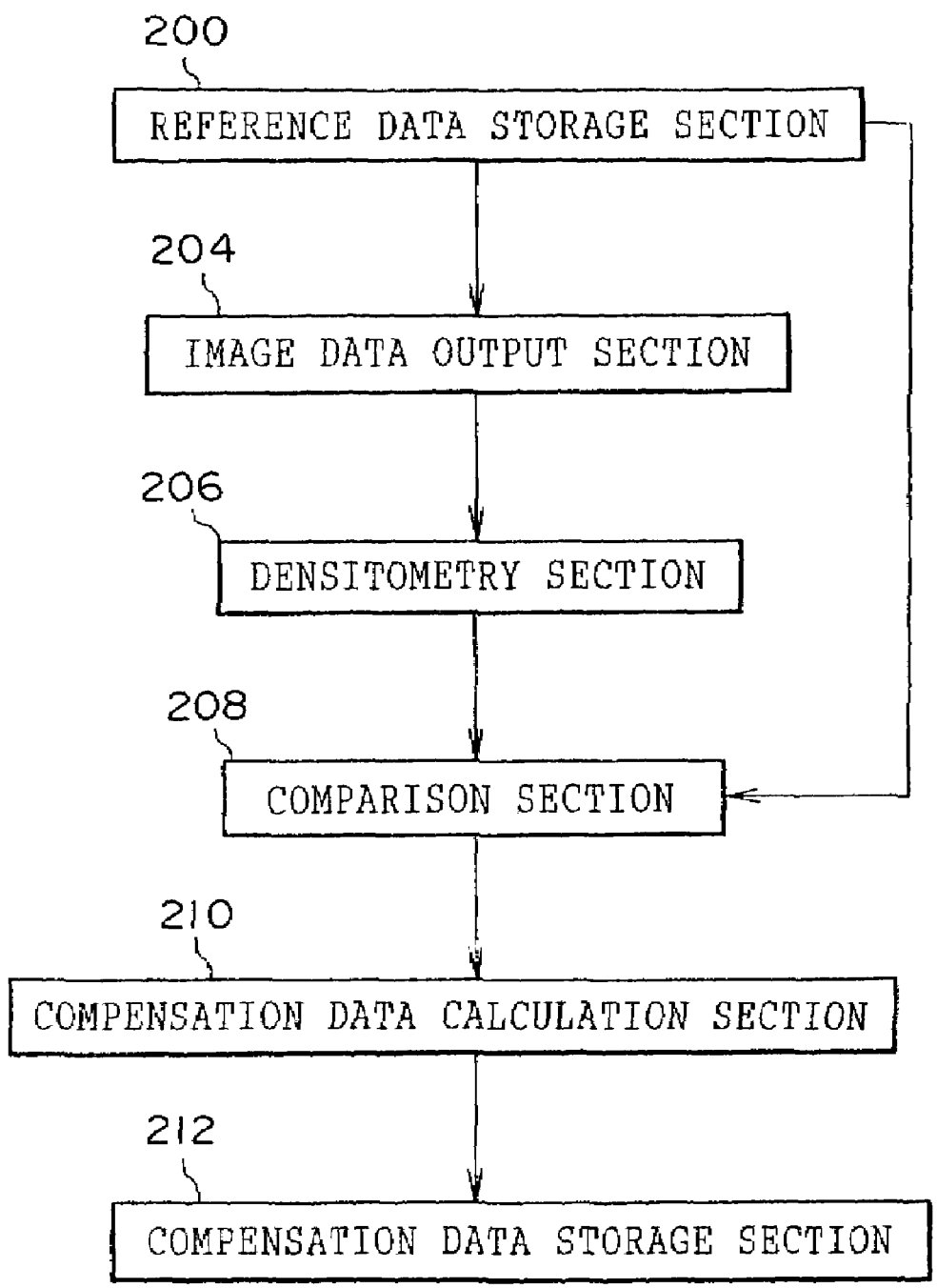
FIG. 3 is a functional block diagram for density measurement relating to the present embodiment.

The image-recording device 10 includes a function for performing calibration, when one or both of the magazines 20 and 92 for the photosensitive material 22 and the image-receiving material 94 is replaced, or by operation at the discretion of a user. FIG. 3 shows densitometry function blocks of the calibration.

Figure 4:
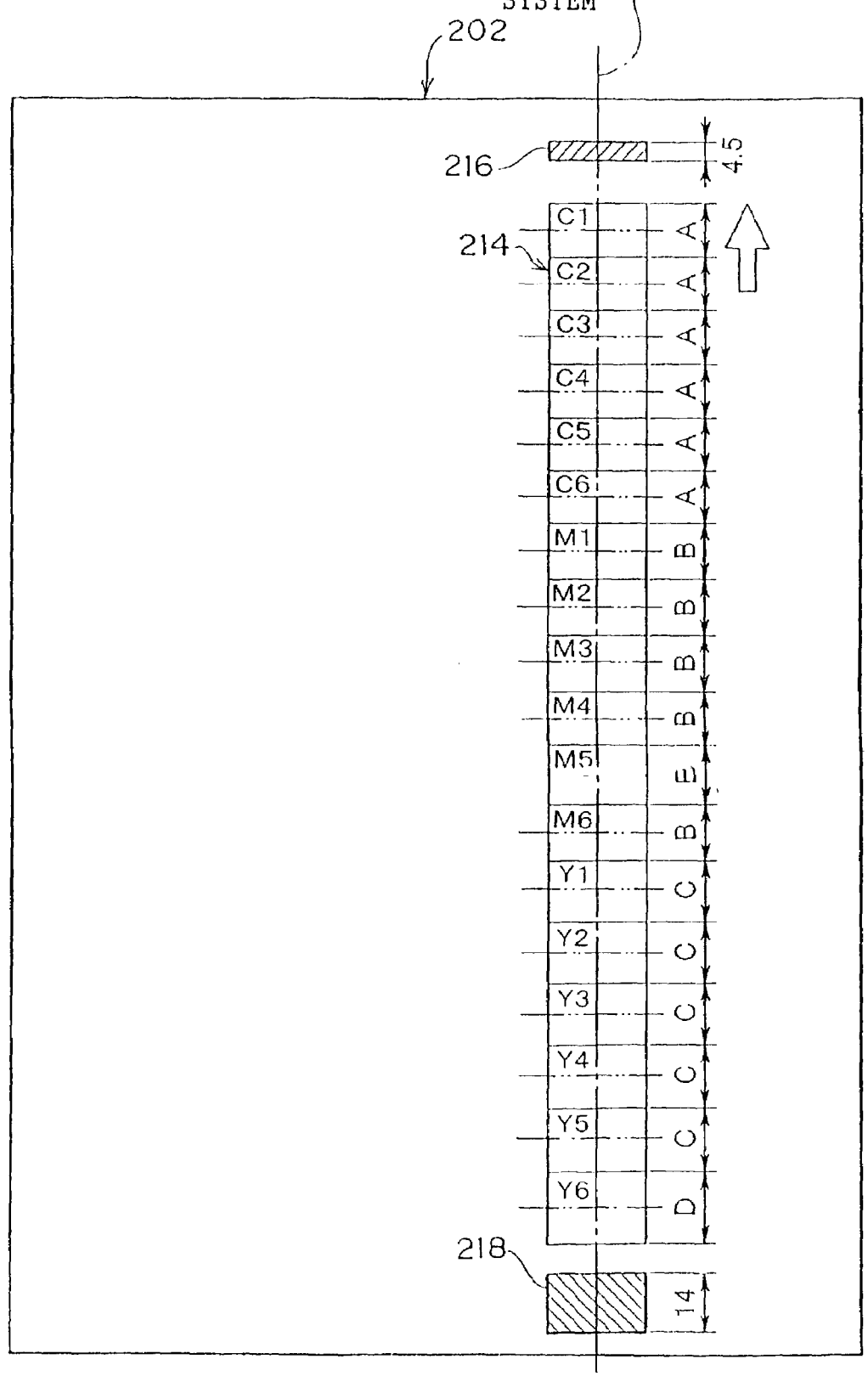
FIG. 4 is a plan view of a color patch chart used in density measurement.

The image-processing section 13 is provided with a reference data storage section 200, in which pre-established standard image data is stored. An image-recording process is performed on the basis of this standard image data. As a result of this process, an image is transferred to a sheet of the image-receiving material 94 and output, to serve as a color patch chart 202, as shown in FIG. 4. The format of the color patch chart 202 is described herebelow.

The standard image data stored in the reference data storage section 200 is sent to an image data output section 204 as image data for image recording. Accordingly, the image-recording device 10 operates and carries out each of processes such as scanning and exposing the photosensitive material 22, heat developing, and transferring to the image-receiving material 94. The image-receiving material 94 is output to serve as the color patch chart 202.

The color patch chart 202 created in the main body of the device is sent to a densitometry section 206, where density data is measured for each patch of each color. The results of this measurement are sent to a comparison section 208. Pre-established standard density data is input to the comparison section 208 from the reference data storage section 200.

Results of comparison at the comparison section 208 are sent to a compensation data calculation section 210. Compensation data is calculated with respect to the standard image data, and stored in a compensation data storage section 212.

FIG. 4 shows the color patch chart 202 in plan view. In the color patch chart 202, a color patch portion 214 is provided with images, with the density of each color being stepwisely adjusted therebetween, arranged in a single band. In the present embodiment, the sequence of these images is six gradation images of cyan (C) from high density to low density (C1 to C6 in FIG. 4), six gradation images of magenta (M) from high density to low density (M1 to M6 in FIG. 4) and six gradation images of yellow (Y) from high density to low density (Y1 to Y6 in FIG. 4). These images are provided in a tight formation, without gaps in between.

Two black reference position indicator patches 216 and 218 are provided at front and back end portions of the band of the color patch portion 214.

A densitometry device 220 is provided at an upper face of the image-recording device 10. At the densitometry device 220, as described later, the color patch chart 202 is fed in and conveyed at a constant speed. When a front end portion of the color patch chart 202 is detected, the conveyance speed is reduced. When the reference position indicator patch 216 at the insertion front end side is detected (actually, when a central portion of the conveyance direction width of the reference position indicator patch 216 is detected, which width may be, for example, 4.5 mm), a pulse count of a pulse motor (stepper motor) is reset. Subsequently, the chart is advanced frame by frame on the basis of predetermined numbers of pulses.

Specifically, each color patch is moved so as to stop at a density measurement position at a time when the frame advance halts. Therefore, any undesired displacement between any of the color patches and the end portion of the color patch chart 202 can be allowed for, and density can be measured at a conveyance direction central position of each color patch.

The purpose of the reference position indicator patch 218 at the conveyance direction back end side is to enable detection of errors, due to slippage or the like, in the frame advance control by the pulse control. Thus, if a difference between a displacement amount according to the pulse control and an actual displacement amount before detection of the back end reference position indicator patch 218 exceeds a difference corresponding to predetermined positions, a conveyance failure is judged to have occurred. A conveyance direction width of the conveyance direction back end reference position indicator patch 218 may be, for example, 14 mm.

Incidentally, in the color patch portion 214 of the present embodiment, the conveyance direction lengths of the color patches are not all equal, but are purposely made to become gradually longer towards the back end. The purpose of this is to allow for conveyance errors of the pulse conveyance control. In other words, the conveyance direction lengths are varied to take account of the way errors will accumulate towards the conveyance direction back end. As shown in FIG. 4, four conveyance direction dimensions, A, B, C and D, are used for the conveyance direction dimensions in the present embodiment. The relationships therebetween are A<B<C<D. Here, imaginary reference lines are established showing positions along the conveyance direction of the color patch chart 202 (the two-dot broken lines in FIG. 4). These lines are perpendicular to the conveyance direction. The patches have the same conveyance direction widths in front of and behind these reference lines. The conveyance direction lengths formed by these widths are the conveyance direction dimensions of the patches. Transverse direction dimensions of the patches are all the same. The conveyance direction dimensions are, specifically, A=13 mm, B=14 mm, C=15 mm, and D=17 mm. The distance from a front end of the color patch chart 202 to a front end edge of the conveyance direction front end reference position indicator patch 216 is 10.25 mm.

The reference position indicator patch 216 and a conveyance direction frontmost color patch of the color patch portion 214 (patch C1 in FIG. 4) are illuminated by light from an LED chip 282, which is described later. If the color of the light irradiated onto the reference position indicator patch 216 and the color of the light irradiated onto the frontmost color patch are the same, the position of the reference position indicator patch 216 may be misread. Accordingly, the below-described LED chip 282 emits light in accordance with the respective colors of the patches, and is provided with light-emitting chips 282R, 282G and 282B, which are described later. Specifically, the light-emitting chips 282R, 282G and 282B are controlled so as to irradiate different colors of emitted light onto the reference position indicator patch 216 and the color patch C1 of the color patch portion 214. Thus, false readings, that is, misreading of the position of the reference position indicator patch 216, can be prevented.

The reference position indicator patch 218 and a conveyance direction rearmost color patch of the color patch portion 214 (patch Y6 in FIG. 4) are also illuminated by light from the below-described LED chip 282. Again, if the color of the light irradiated onto the reference position indicator patch 218 and the color of the light irradiated onto the rearmost color patch are the same, the position of the reference position indicator patch 218 may be misread. Accordingly, the below-described LED chip 282 emits light in accordance with the respective colors of the patches, and is provided with the below-described light-emitting chips 282R, 282G and 282B. Specifically, the light-emitting chips 282R, 282G and 282B are controlled so as to irradiate different colors of emitted light onto the reference position indicator patch 218 and the color patch Y6 of the color patch portion 214. Thus, false readings, that is, misreading of the position of the reference position indicator patch 218, can be prevented.

Figure 5:
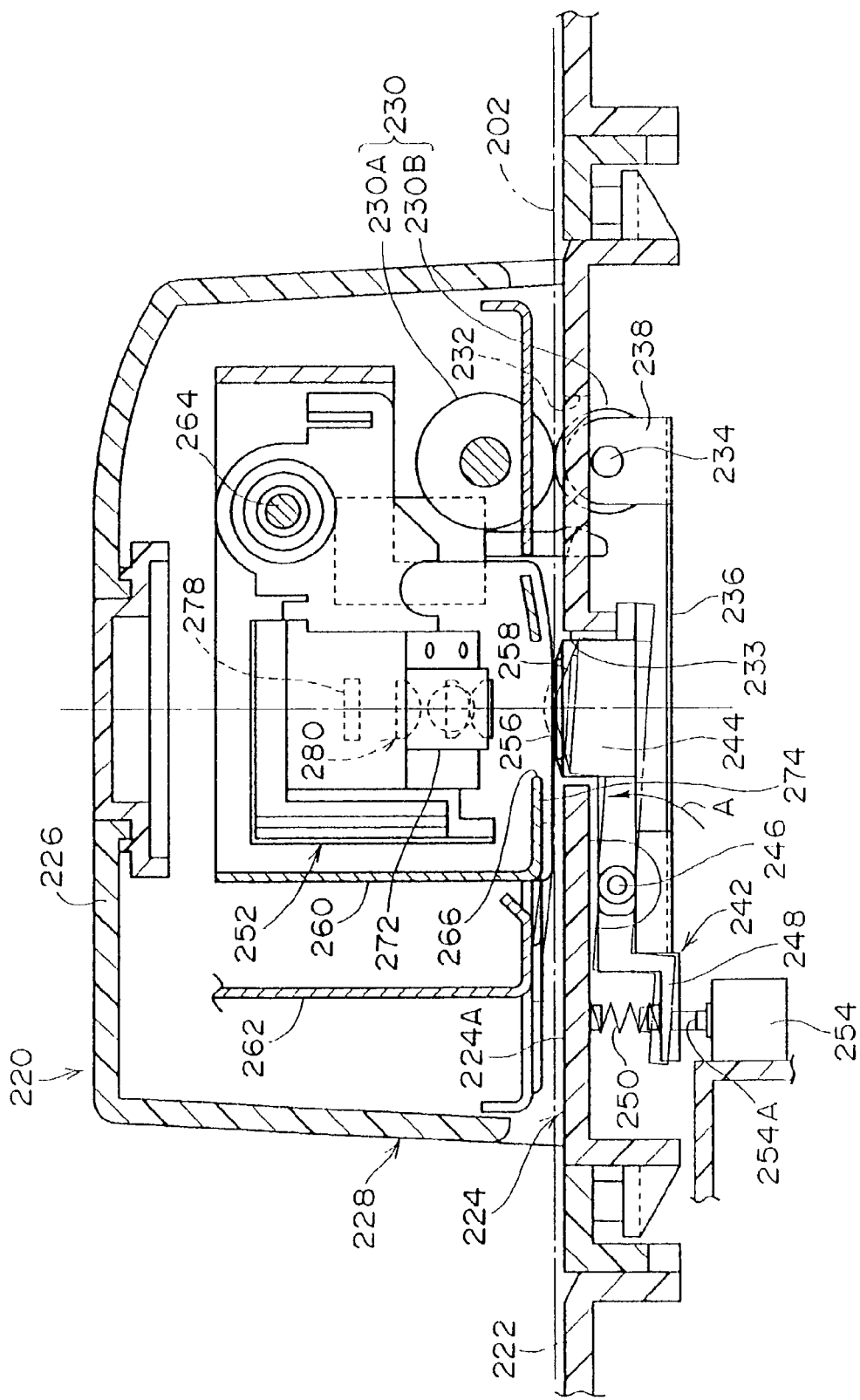
FIG. 5 is a sectional side view of a densitometry device relating to the present embodiment.

As shown in FIG. 5, the densitometry device 220 is disposed at a flat surface portion 222 provided at an upper surface panel of the image-recording device 10. The densitometry device 220 is structured with a base portion 224, a cover 226 and a main body portion 228. The main body 228 is attached to an upper portion of the base portion 224 and is covered by the cover 226.

As shown in FIG. 5, an attachment portion for the densitometry device 220 on the flat surface portion 222 is recessed in a substantially rectangular shape, into which the base portion 224 of the densitometry device 220 is inserted.

A boundary portion between the base portion 224 and the main body portion 228 is substantially coplanar with the flat surface portion 222, and forms a conveyance path for the color patch chart 202.

Figure 8:
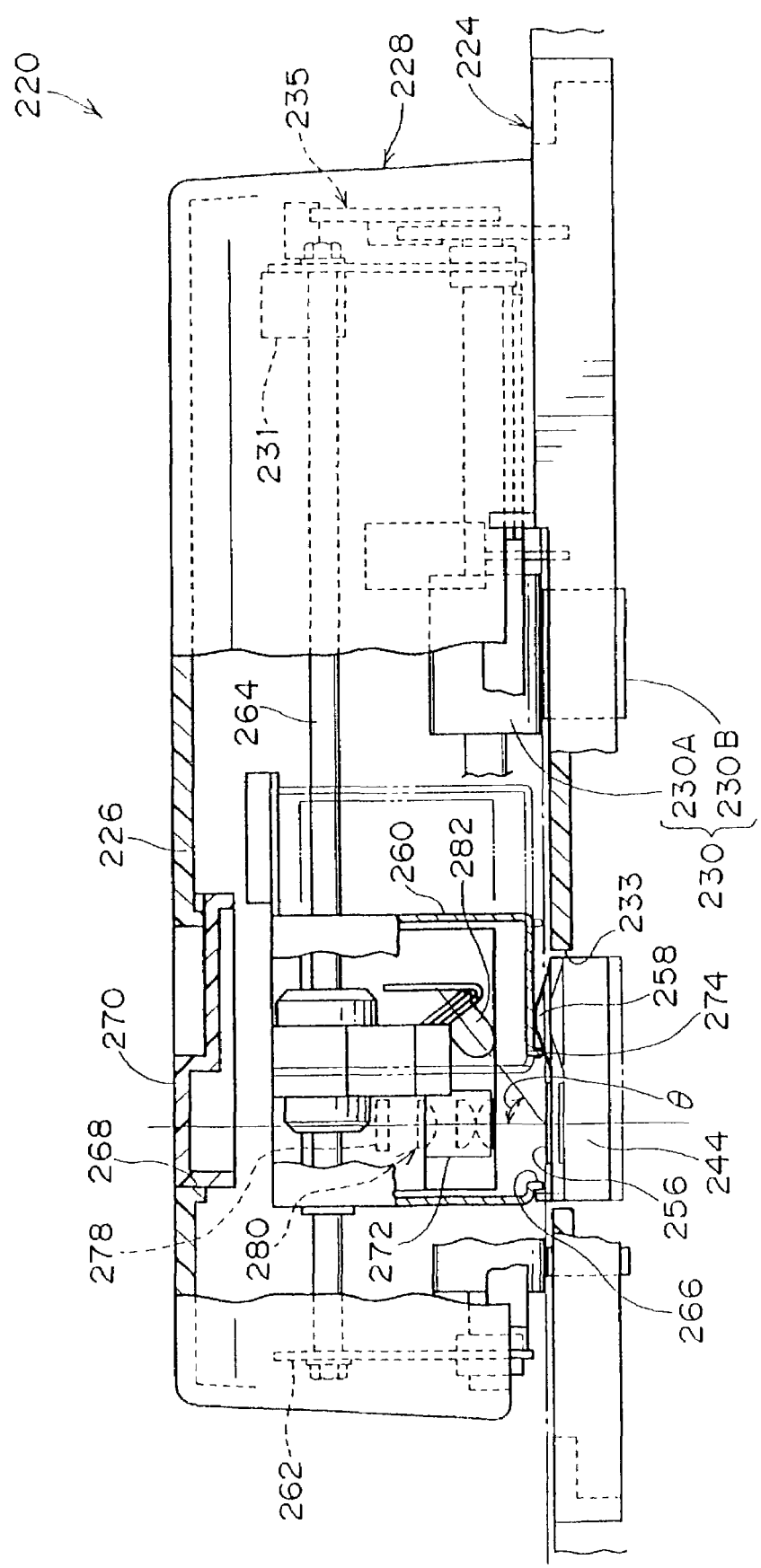
FIG. 8 is a front view of a main body of the densitometry device as viewed along a conveyance direction.

Pairs of conveyance rollers 230 are provided at an upstream end side of this conveyance path. The conveyance rollers 230 are upper rollers 230A, which are attached at the main body portion 228 side, and lower rollers 230B, which are attached at the base portion 224 side. The upper rollers 230A are driving rollers, which are rotated by driving force of a motor 231 (see FIG. 8) via a gear unit 235 (FIG. 8). The lower rollers 230B are driven rollers.

Figure 6:
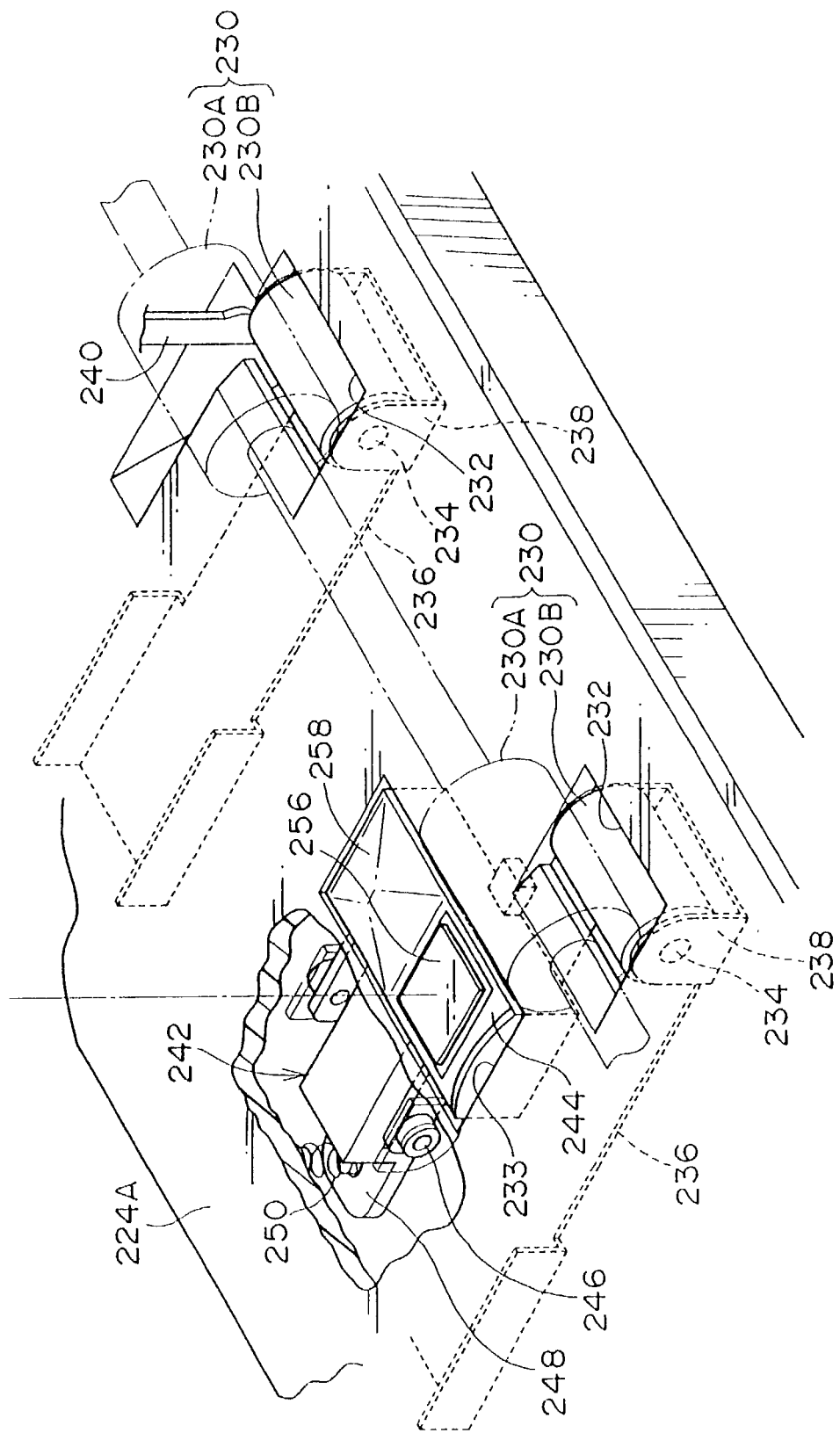
FIG. 6 is a perspective view showing an interior portion of the densitometry device relating to the present embodiment.

As shown in FIG. 6, the lower rollers 230B are divided between two positions, which are equally spaced from a central portion of a color patch chart conveyance direction transverse direction, at an upper surface (conveyance support surface) of the base portion 224. Rectangular holes 232 are provided in the upper surface of the base portion 224 in correspondence to these two positions.

Figure 7:
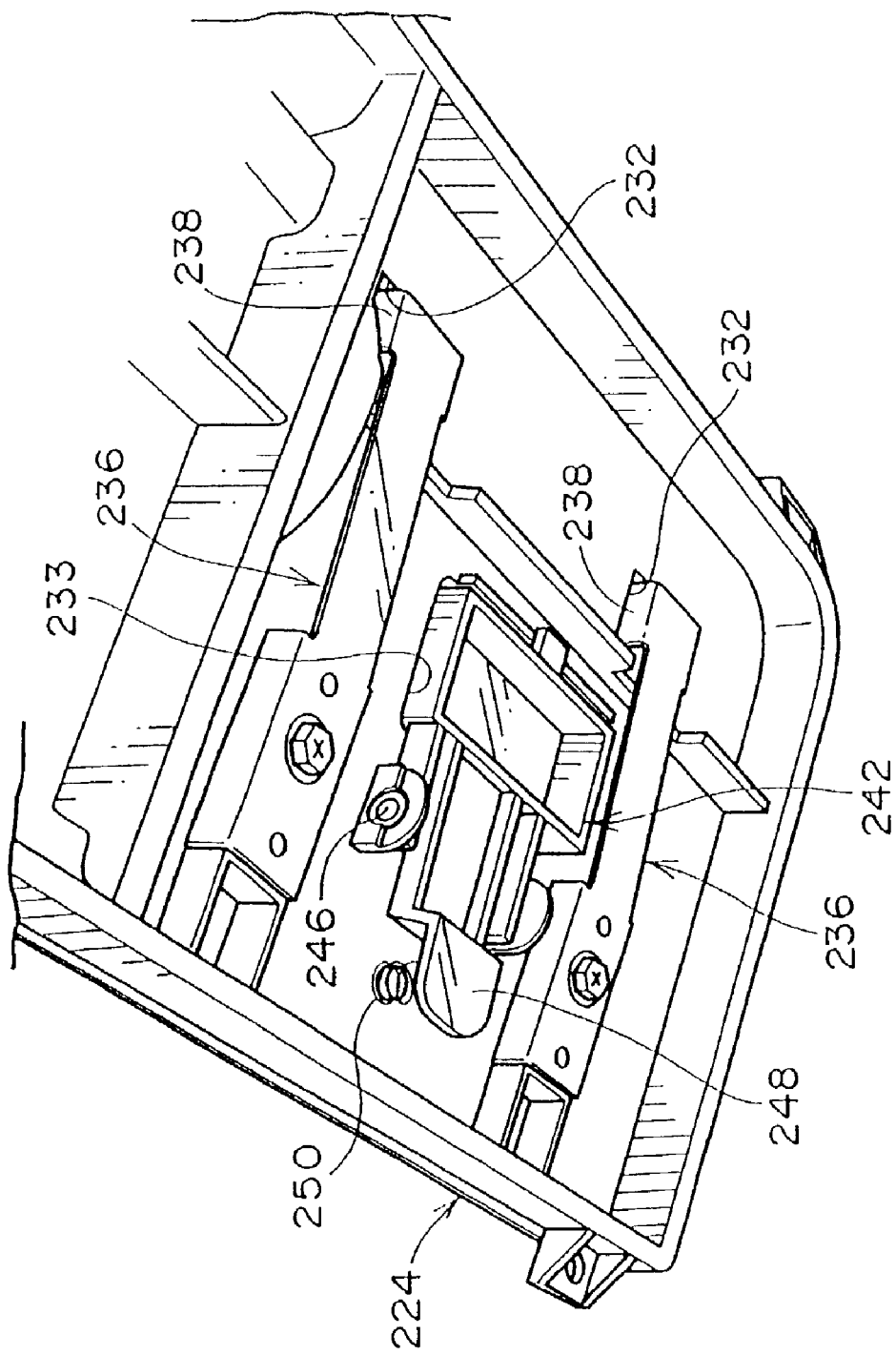
FIG. 7 is a perspective view of the densitometry device as viewed from a rear side of a base portion.

As shown in FIGS. 5 to 7, each of the pair of lower rollers 230B has a rotation axis 234. Each rotation axis 234 is supported by a plate spring bracket 236. One end portion of each plate spring bracket 236 is fixed to the base portion 224. A distal end portion of each plate spring bracket 236 is provided with an axis-receiving portion 238 formed with a substantially U-shaped cross-section, at which the corresponding rotation axis 234 is rotatably supported. Thus, each of the pair of lower rollers 230B is urged to protrude from the rectangular hole 232 by urging force of the corresponding plate spring bracket 236. That is, the pair of lower rollers 230B is provided in correspondence with the pair of upper rollers 230A, and contacts the pair of upper rollers 230A with a predetermined pressure (nipping force). Consequently, the color patch chart 202 is conveyed at fixed speed by driving force of the conveyance roller pairs 230.

A contact terminal 240 of an unillustrated limit sensor protrudes from the main body portion 228 slightly downstream from the conveyance roller pairs 230. This contact terminal 240 is rotated by contact with the front end of the color patch chart 202, and switches the limit sensor on and off. As a result, the front end of the color patch chart 202 can be detected by a signal from the limit sensor.

A substantially rectangular hole 233 is formed in the conveyance support surface, slightly downstream along the conveyance path from the pair of lower rollers 230B. The rectangular hole 233 corresponds to a conveyance path of the band-shaped color patch portion 214 of the color patch chart 202 (see FIG. 4).

As shown in FIG. 5, a pressing portion 244 of a pressing plate 242 is disposed in the rectangular hole 233. The pressing plate 242 extends downstream in the conveyance direction from the pressing portion 244. A central portion of the pressing plate 242 is rotatably supported by the base portion 224 via an axis 246. A proximal end portion of the pressing plate 242 is formed into a substantially L-shaped tongue portion 248. A predetermined gap is formed between the tongue portion 248 and a rear face side of a conveyance support surface 224A of the base portion 224. A compression coil spring 250 is disposed in this gap. One end of the compression coil spring 250 abuts against a rear face side of the conveyance support surface 224A, and the other end abuts against the tongue portion 248. Thus, the pressing plate is rotated about the central portion in the direction of arrow A (see FIG. 5) by urging force of the compression coil spring 250. Consequently, the pressing portion 244 protrudes from the hole 233 and is pushed up beyond the conveyance support surface 224A.

Hence, when the color patch chart 202 is on the conveyance support surface 224A, the color patch chart 202 is pushed up from the conveyance support surface 224A and can abut against a densitometry unit 252. In other words, the pressing portion 244 functions to eliminate a gap between the color patch chart 202 and the densitometry unit 252.

A solenoid 254 is provided at an image-recording device main body side of the pressing plate 242. An actuator 254A of the solenoid 254 opposes a lower surface of the tongue portion 248 of the pressing plate 242 (that is, a rear surface with respect to a surface thereof that abuts against the compression coil spring 250). When the color patch chart 202 is conveyed, the actuator 254A is extended. Thus, the urging force of the compression coil spring 250 is opposed, the pressing plate 242 is rotated about the axis 246 at the central portion in a direction opposite to the direction of arrow A (see FIG. 5), and the pressing portion 244 is submerged in the rectangular hole 233. When the color patch chart 202 is not being conveyed (that is, when density is being measured), the actuator 254A is withdrawn and the urging force of the compression coil spring 250 is allowed to take effect on the pressing portion 244 (refer to the imaginary line positions in FIG. 5).

As shown in FIG. 6, a white plate 256 is attached to the pressing portion 244. This plate 256 is used as a standard for white balance adjustment of the densitometry unit, which is described later.

A guide protrusion portion 258 is also provided on the pressing plate 242, at the pressing portion 244. The guide protrusion portion 258 is formed with a protrusion in a substantially square pyramid shape. The function of the guide protrusion portion 258 is described later.

As shown in FIG. 5, a bracket 262, which holds a housing of the densitometry unit 252, is provided in the main body portion 228. The bracket 262 is fixed in a state of being accommodated by the cover 226, which covers the main body portion 228. The rotation axes of the upper rollers 230A are rotatably supported at the bracket 262. Also, the motor 231 and gear unit 235, which are the drive source for the upper rollers 230A, are assembled to the bracket 262 (see also FIG. 8).

The housing 260 is formed of a conductive synthetic resin. Thus, undesired effects of noise on a photoelectric conversion element 278 and the like (described later) that are installed at the housing 260 are attenuated.

As shown in FIG. 8, a shaft 264 is attached to the bracket 262. The axial direction of the shaft corresponds to the conveyance transverse direction of the color patch chart 202. The densitometry unit 252 is supported at the shaft 264. As a result, the densitometry unit 252 is movable along the axial direction of the shaft 264 (the left-right direction in FIG. 8). The densitometry unit 252 can be positioned at at least two positions, a densitometry position and a withdrawal position.

Here, the pressing portion 244 of the pressing plate 242 is near a measurement aperture portion 266 provided in the housing 260 of the densitometry unit 252. In this state, when the densitometry unit 252 moves along the shaft 264, the housing 260 and the guide protrusion portion 258 provided on the pressing portion 244 interfere with each other. Therefore, when the densitometry unit 252 moves, the housing 260 pushes down the pressing portion 244 (see the imaginary line positions in FIG. 8), and thus any application of excessive force (in the conveyance transverse direction) to the pressing portion 244 is prevented.

Figure 9:
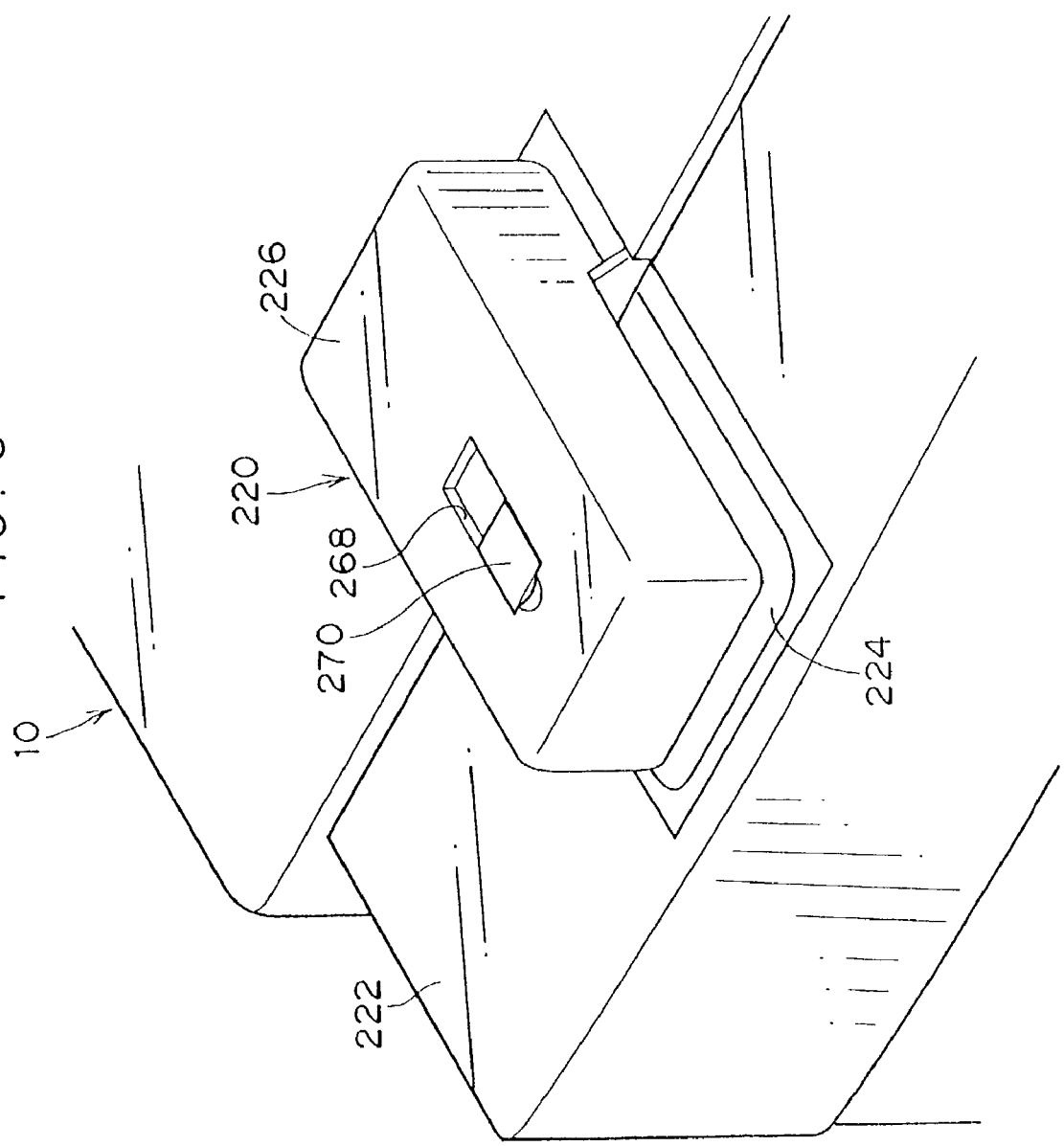
FIG. 9 is an enlarged perspective view showing an upper surface of a density measurement portion.

When the housing 260 of the densitometry unit 252 is moved along the shaft 264 to the withdrawal position, the white plate 256 of the pressing portion 244 is directly exposed through an aperture portion 268 of the cover 226. A space through the aperture portion 268 to the plate 256 can be used as an operation space for wiping soiling from the plate 256. As shown in FIG. 9, a slideable closing cover 270 is provided at the aperture portion 268. The closing cover 270 and the housing 260 are linked at an interior portion (this linkage is not illustrated). Consequently, when this cover has been closed, the housing 260 can be moved to the densitometry position, and when the cover has been opened, the housing 260 can be moved to the withdrawal position.

Figure 10:
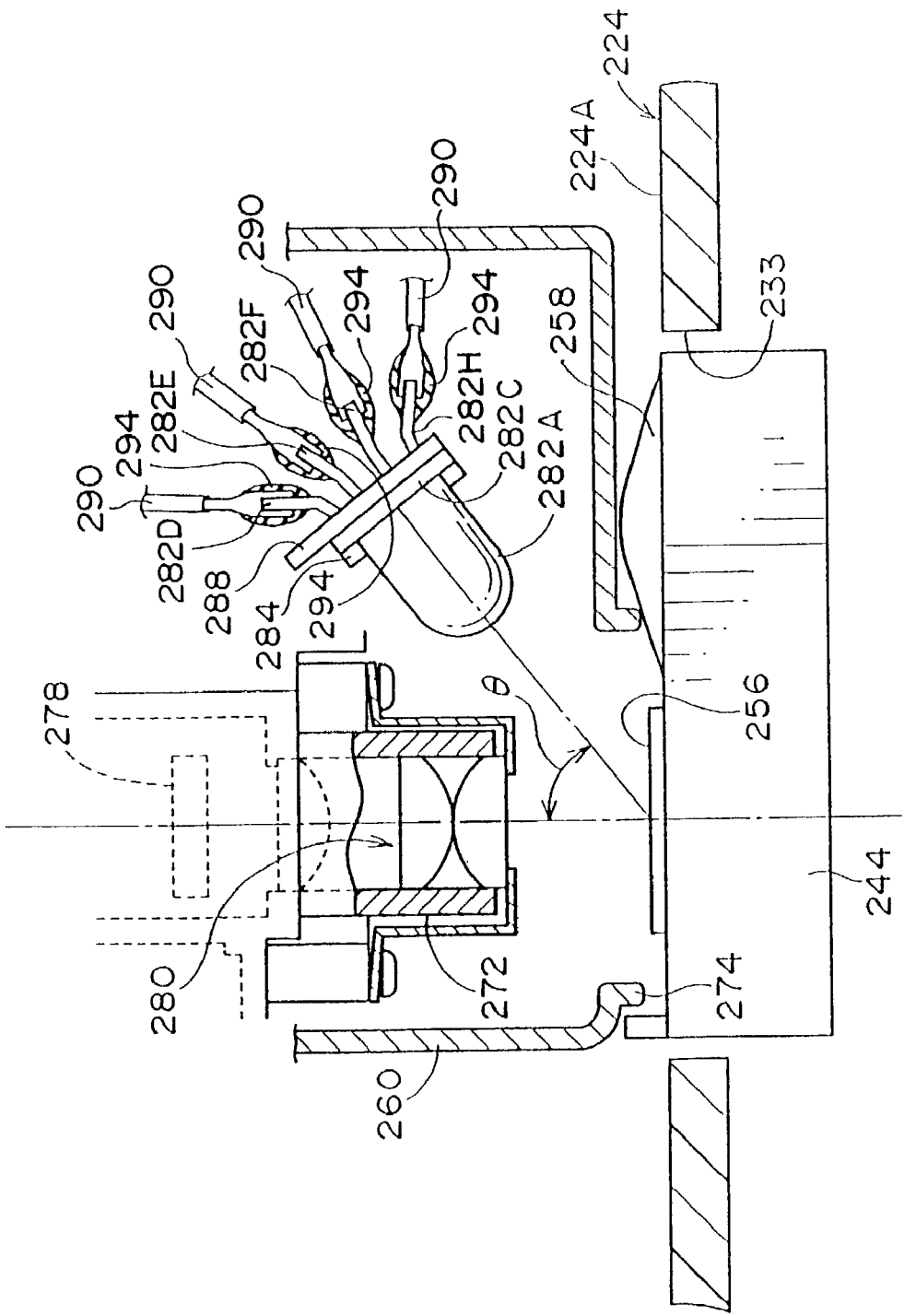
FIG. 10 is a sectional view showing internal structure of a density measurement unit.

FIG. 10 shows structure inside the housing 260 of the densitometry unit 252.

A barrel portion 272 is provided inside the housing 260. A protrusion-contact portion 274 is provided at an end portion side of the barrel portion 272 that faces the base portion 224. The protrusion-contact portion 274 is integral with the housing 260 and structures the periphery of the measurement aperture portion 266. Because of the urging force of the compression coil spring 250, the pressing portion 244 abuts against the protrusion-contact portion 274.

As shown in FIG. 13, one end portion of the barrel portion 272 is disposed at a position slightly inside from the measurement aperture portion 266 of the protrusion-contact portion 274.

The photoelectric conversion element 278 is attached near an aperture at the other end of the barrel portion 272. A plural lens group 280 is disposed downward of the photoelectric conversion element 278. The protrusion-contact portion 274 is positioned at a focal point according to the optical effects of the lens group 280. The lens group 280 and photoelectric conversion element 278 structure a density measurement optical system.

The LED chip 282, which serves as a light source, is disposed between the one end of the barrel portion 272 and the protrusion-contact portion 274. A reference optical axis of the LED chip 282 passes through the measurement aperture portion 266 of the protrusion-contact portion 274.

In the present embodiment, an angle $\theta$ between the reference optical axis of the LED chip 282 and an optical axis, according to the photoelectric conversion element 278, of the density measurement optical system (an illumination angle) is set to 52°. The angle $\theta$ is set in a range such that a light amount required for measuring density at the photoelectric conversion element 278 is assuredly provided when one LED chip 282 is caused to illuminate by a predetermined voltage, and such that light from the LED chip 282 that has been reflected or transmitted at the surface of the color patch chart 202 is not directly incident on the photoelectric conversion element 278. This allowable range is 47° to 55° (as explained below).

Figure 14:
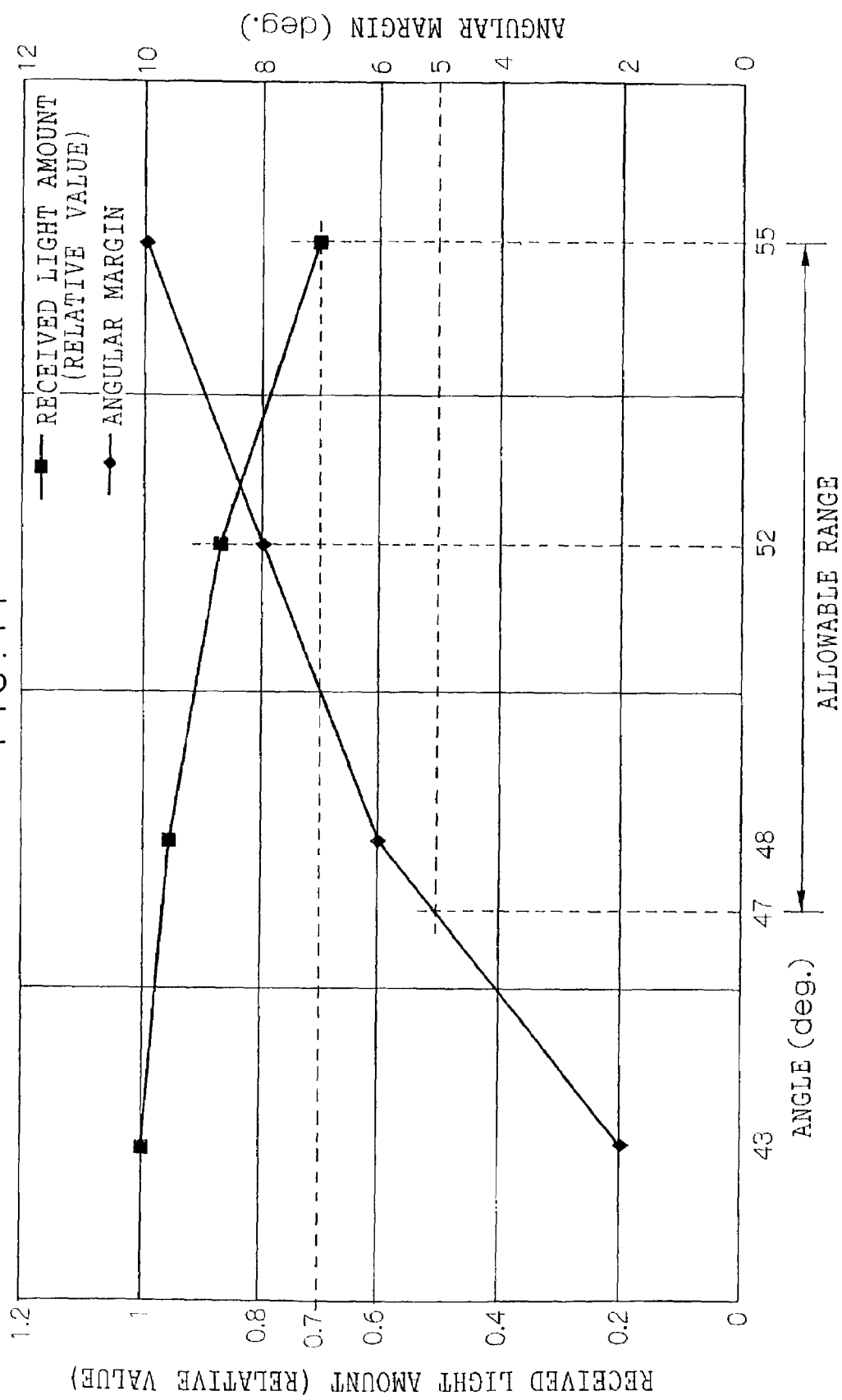
FIG. 14 shows a graph showing amounts of light received by a photoelectric conversion element with respect to angle between a reference line, which is an optical axis of an LED chip, and an optical axis, according to a photoelectric conversion element, of a density measurement optical system (that is, an axis of a barrel), and a graph showing angular margins with respect to the same angle.

FIG. 14 shows graphs of relationships between the angle $\theta$ and received light amounts of the photoelectric conversion element 278, and between the angle $\theta$ and angular margins.

Herein, "angular margin" means, when the color patch chart 202 is being inclined at set angles with respect to the optical axis of the density measurement optical system, a first angle of inclination at which light that is regularly reflected from the color patch chart 202 will be incident on the density measurement optical system.

Because the angle $\theta$ is greater than 45° in the present embodiment, the received light amount that is received by the photoelectric conversion element 278 varies with changes in the value of the angle $\theta$. Further, a signal-to-noise ratio (SNR) of signals output from the photoelectric conversion element 278 during density measurement varies in accordance with variations in the received light amount. Changes in the SNR are particularly significant when high densities are being measured. Therefore, when measuring high densities, a range of variation of the SNR should be kept as small as possible. In order to keep this range of variation small, it is preferable to obtain received light amounts of not less than 70% of a light amount that would be received with an angle $\theta$ of 45°. Accordingly, in the present embodiment, in order to obtain received light amounts of at least this 70%, the angle $\theta$ is kept to 55° or less. The reason for taking the case of θ being 45° as a reference point is that the angle θ is often set to 45° in usual densitometry devices.

When the color patch chart 202 is being conveyed, conveyance irregularities may occur, in which there are variations in a normal direction of the surface of the color patch chart on which the patches are formed. Due to these variations, an angle of incidence (inclination angle), which is the angle between the normal line of the surface on which the patches are formed and the reference optical axis of the LED chip 282, changes. Due to such a change in the angle of incidence, an angle of reflection at the color patch chart 202 of light emitted from the LED chip 282 also changes. Because the angle of reflection changes, light that has been reflected from the color patch chart 202 may be directly incident on the photoelectric conversion element 278. In the present embodiment, in order that accurate density measurements can be carried out even in the presence of conveyance irregularities of the color patch chart 202, and of assembly errors introduced during manufacture, an angular margin is preferably not less than 5°. Therefore, to keep the angular margin at 5° or above, the angle θ in the present embodiment is at least 47°.

For such reasons, the allowable range is 47 to 55°.

Figure 11A:
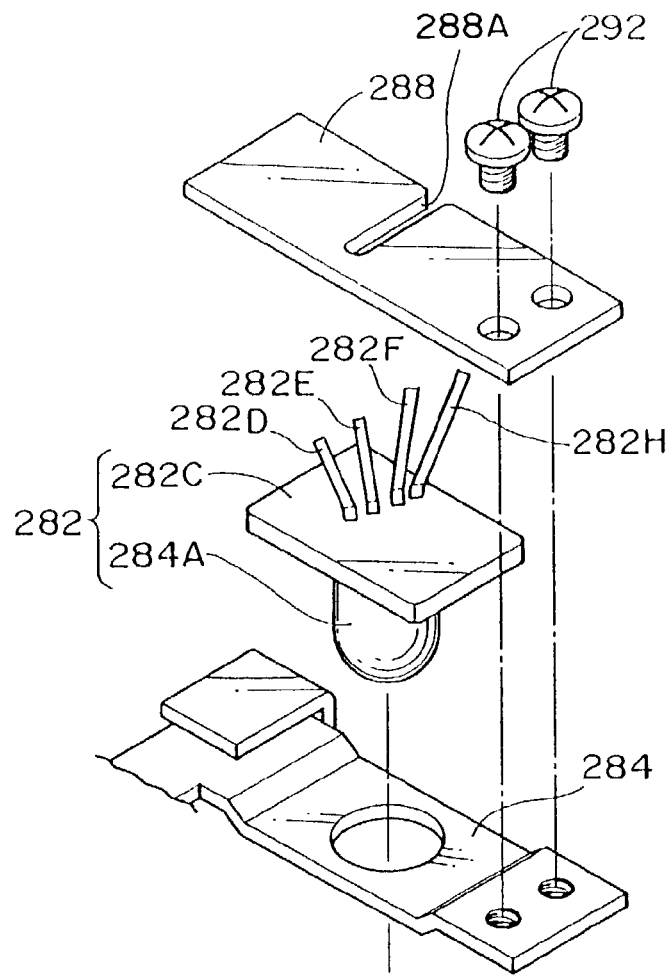
FIG. 11A is an exploded perspective view showing how an LED chip is assembled.
Figure 11B:
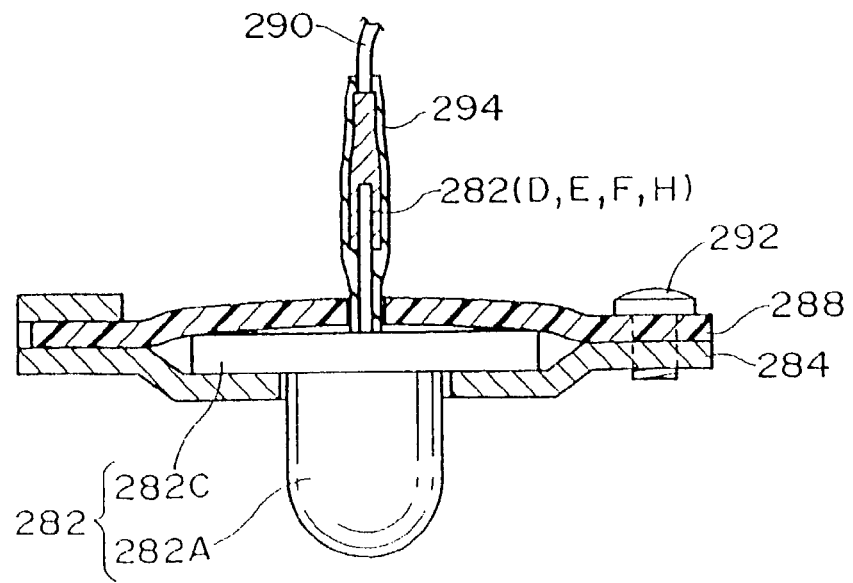
FIG. 11B is a side sectional view of the LED chip after assembly.

The angle θ is determined by assembly of the LED chip 282 to the housing 260. That is, as shown in FIGS. 11A and 11B, a holding plate 284 which holds the LED chip 282 is integrally formed at the housing 260 in advance such that a normal line of the holding plate 284 is at an angle of from 47° to 55° with respect to the axis of the barrel portion 272, that is, 52° in the present embodiment. By thus forming integrally the holding plate 284 and the housing 260, the angle θ between the reference optical axis of the LED chip 282 and the optical axis, according to the photoelectric conversion element 278, of the density measurement optical system (that is, the axis of the barrel) can be set.

Figure 12A:
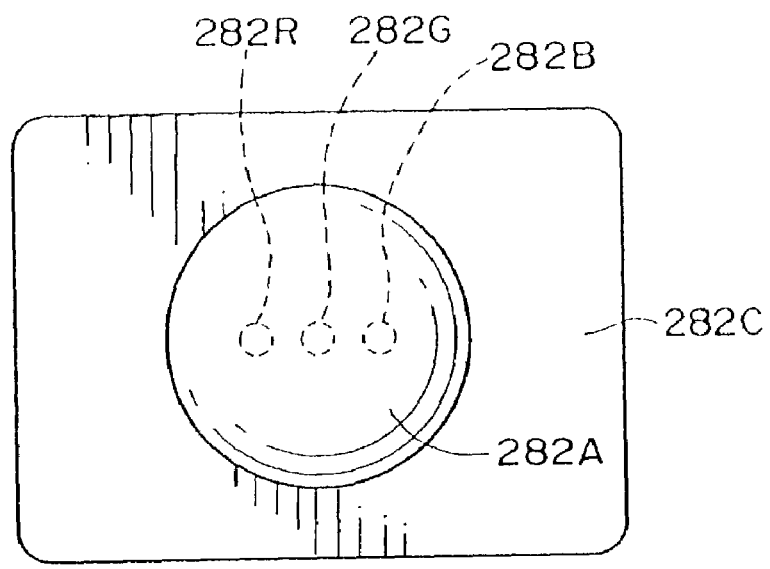
FIG. 12A is a front view of the LED chip.
Figure 12B:
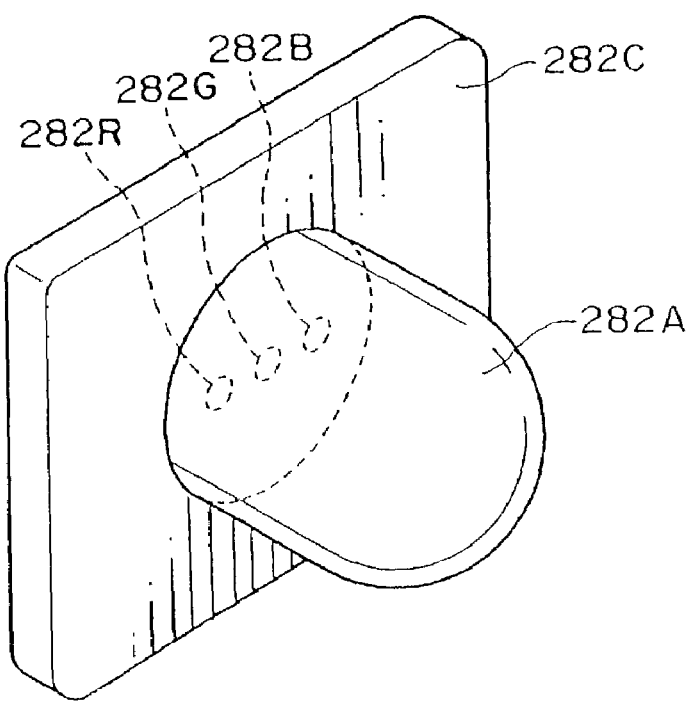
FIG. 12B is a perspective view of a base plate attached to a light-emitting portion.

As shown in FIGS. 12A and 12B, the LED chip 282 is provided with light-emitting chips 282R, 282G and 282B, which emit red, green and blue light, inside a substantially cannon shell-shaped light-emitting portion 282A. Hence, because the LED chip 282 can emit lights of mutually different colors, the LED chip 282 can be used for measuring densities on an object of measurement on which a color image is formed. The light-emitting chips 282R, 282G and 282B are arranged in line with the conveyance direction of the color patch chart 202. Therefore, inclination angles of the light-emitting chips 282R, 282G and 282B with respect to the measurement axis of the density measurement optical system will always change consistently with each other, and no difference between the inclination angles of the different colors will be caused. Further, amounts of light emitted onto the color patch chart 202 may be supplemented by providing a plurality of the light emitting chip 282, which may each emit the same colors.

A substantially round hole 286 is formed in the holding plate 284. The light-emitting portion 282A of the light-emitting chip 282 is accommodated at the round hole 286. A substantially rectangular base plate 282C is attached at a base portion of the light-emitting chip 282. The base plate 282C serves as a stopper, and determines the extent of insertion of the light-emitting portion 282A into the round hole 286.

As shown in FIGS. 11A and 11B, three terminals 282D, 282E and 282F, which are for causing emission of light of the respective colors, lead out from a rear surface portion of the base plate 282C. An earth terminal, which is common to these three terminals, also leads out from this rear surface portion. The LED chip 282 is restrained at the base plate 282C rear surface portion side by a restraining plate 288. The restraining plate 288 intrinsically functions as a plate spring. Thus, the LED chip 288 is held in position relative to the holding plate 284.

Leads 290 are connected in correspondence to the four terminals 282D, 282E, 282F and 282H. A slit-like cutaway portion 288A is formed in the restraining plate 288 such that the restraining plate 288 does not obstruct the terminals 282D, 282E, 282F and 282H.

One end of the restraining plate 288 is engaged with part of a connecting portion that connects the housing 260 to the holding plate 284. Another end of the restraining plate 288 is screwed to the holding plate 284 by screws 292 or the like. Thus, the restraining plate 288 is fixed.

For insulation, insulation tubes 294 cover connection portions that connect the terminals 282D, 282E, 282F and 282H with the leads 290. As a result, when the insulation tubes 294 have been put on the connection portions, the outer diameters of the portions are larger than a usual pitch between the terminals of the LED chip 282 would be. Therefore, if the terminals 282D, 282E, 282F and 282H are in usual positions, the insulation tubes 294 will be close together, and will interfere with one another. Accordingly, in the present embodiment, the terminals 282D, 282E, 282F and 282H are slanted along the direction in which the terminals 282D, 282E, 282F and 282H are lined up.

In the present embodiment, when the terminals 282D, 282E, 282F and 282H are slanted as described above, the terminals 282D, 282E, 282F and 282H are bent at portions thereof at the side at which they are connected to the leads 290. Generally, when the terminals 282D, 282E, 282F and 282H are bent, there is stress in the terminals 282D, 282E, 282F and 282H. If the terminals 282D, 282E, 282F and 282H are bent at base plate 282C side end portions thereof, the stress will be concentrated in those end portions. Therefore, in the present embodiment, the terminals 282D, 282E, 282F and 282H are bent from partway along the side at which they are connected to the leads 290. Therefore, there is less concentration of stress in the terminals than in a case in which the terminals 282D, 282E, 282F and 282H are bent at the base plate 282C side end portions thereof.

That is, in the present embodiment, each of the terminals 282D, 282E, 282F and 282H is canted in a direction along the direction in which the terminals 282D, 282E, 282F and 282H are arranged, from partway along the side at which each terminal is connected to the lead 290. Consequently, the pitch between the terminals can be made larger, at least for positions at which the insulation tubes 294 are provided, and interference between the insulation tubes 294 is suppressed. Here, the terminals 282D, 282E, 282F and 282H may be alternately slanted in different directions. However, in view of ease of assembly and the like, it is more effective to slant all the terminals along the direction in which the terminals are lined up.

Figure 15A:
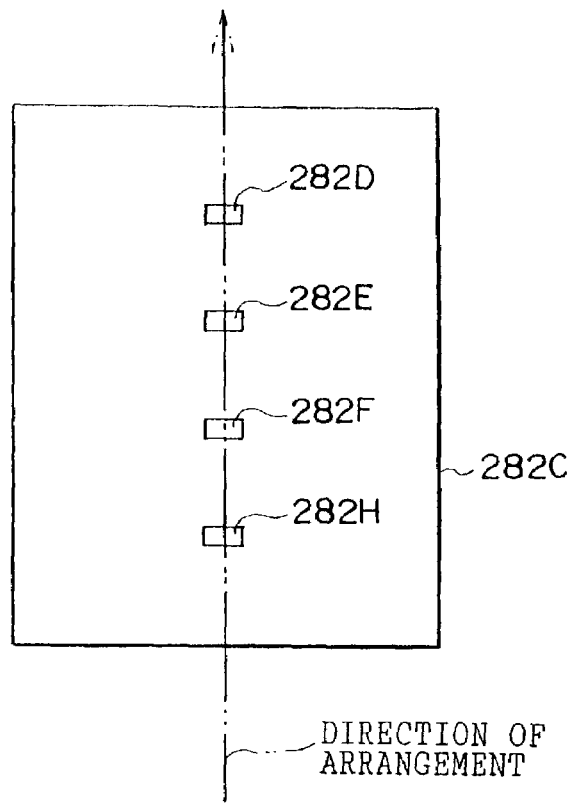
FIG. 15A is a top view of a substrate on which terminal positions are arranged in a straight line.
Figure 15B:
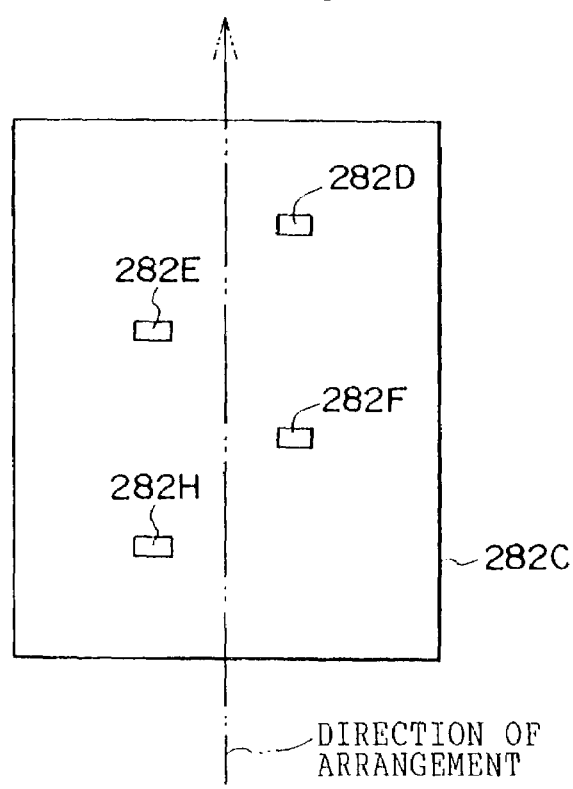
FIG. 15B is a top view of a substrate on which terminal positions are arranged in a staggered pattern.

FIGS. 15A and 15B show positions of the terminals 282D, 282E, 282F and 282H on the base plate 282C. The direction of arrangement of the terminals 282D, 282E, 282F and 282H is shown in FIGS. 15A and 15B by broken line arrows.

In the present embodiment, as shown in FIG. 15A, the terminals 282D, 282E, 282F and 282H are arranged on the base plate 282C in a single straight line along the arrangement direction. However, as shown in FIG. 15B, the terminals 282D, 282E, 282F and 282H may be arranged on the base plate 282C in a staggered pattern along the arrangement direction. As another alternative, the connection portions of the terminals 282D, 282E, 282F and 282H may be slanted in a pattern radiating from the arrangement direction.

Operation of the present embodiment is described below.

When image signals are inputted from the image-processing section 13, predetermined image processing is begun. Then, an image magnification for recording, a number of copies to be processed and the like are specified. When commencement of recording is instructed, the light beam irradiates onto the photosensitive material 22, main scanning is carried out, and image processing is begun.

Provided the photosensitive material magazine 20 has been installed, the nip rollers 24 operate and the photosensitive material 22 is drawn out by the nip rollers 24 at a speed of, for example, 50 mm/sec. When a predetermined length of the photosensitive material 22 has been drawn out, the cutter 26 operates and cuts the photosensitive material 22 to the predetermined length. The photosensitive material 22 is further conveyed by the conveyance rollers 28 and 30 at a speed of, for example, 50 mm/sec. Then, the photosensitive material 22 that has been conveyed by the conveyance rollers 28 and 30 is passed through the exposure section 34 by the conveyance rollers 36 and 38, at a predetermined speed of, for example, 50 mm/sec. When the photosensitive material 22 is passing through the exposure section 34, an exposure device 40 operates.

The exposure section 34 is disposed between the conveyance rollers 36 and the conveyance rollers 38. When the photosensitive material 22 passes through the exposure section (an exposure point) between these conveyance rollers, the light beam controlled by the image-processing section 13 is scanned in a direction intersecting the conveyance direction (main scanning).

The photosensitive material 22 that has been exposed by the exposure device 40 is temporarily sent into the switchback 70. Then, by reverse rotation of the conveyance rollers 36, 38 and 30, the photosensitive material 22 is again passed through the exposure section 34, and fed through the junction portion 74 into the water-coating section 72.

The photosensitive material 22 that has been fed to the water-coating section 72 is fed in between the guide plate 82 and the coating tank 76 by driving of the feed rollers 78, and the squeeze rollers 80 grippingly convey the photosensitive material 22 further. Thus, while passing through the water-coating section 72, the photosensitive material 22 is coated with water, and then excess water is removed by the squeeze rollers 80. The photosensitive material 22, having thus been coated with a solvent for image formation, water, at the water-coating section 72, is sent into the heat development and image transfer section 90 by the squeeze rollers 80.

Meanwhile, in correspondence with the commencement of scanning exposure of the photosensitive material 22, the image-receiving material 94 is drawn out of the image-receiving material magazine 92 by the nip rollers 96 and conveyed. When a predetermined length of the image-receiving material 94 has been drawn out, the cutter 98 operates and cuts the image-receiving material 94 to the predetermined length. The image-receiving material 94 that has been cut by the cutter 98 is conveyed by the conveyance rollers 100 and 102 while being guided by the guide plates 104A and 104B, and is put into a waiting state just upstream of the heat development and image transfer section 90.

At the heat development and image transfer section 90, the photosensitive material 22 is fed in, between the outer periphery of the heating drum 110 and a laminating roller 114, by the squeeze rollers 80. When this feeding is detected, conveyance of the image-receiving material 94 is resumed. The image-receiving material 94 is fed in to the laminating roller 114, and the heating drum 110 operates. As a result, the photosensitive material 22 and the image-receiving material 94 are superposed by the laminating roller 114. In this state, the photosensitive material 22 and the image-receiving material 94 are sandwiched between the heating drum 110 and the endless pressure belt 112, are conveyed around close to half of the circumference of the heating drum 110 (between a winding roller 120 and another winding roller 126), and are heated. Because the photosensitive material 22 is heated during this gripping conveyance time, and during a stopped time, a mobile colorant is released therefrom. At this time, this colorant is transferred to a colorant-fixing layer of the image-receiving material 94. Thus, an image is obtained.

Thereafter, the photosensitive material 22 and image-receiving material 94 are grippingly conveyed to the curve guide roller 132 at the side of the heating drum 110. When the photosensitive material 22 and image-receiving material 94 reach the curve guide roller 132, the separation pawl 134 is moved by the cam 116. The distal end portion of the photosensitive material 22, which projects distally further than the image-receiving material 94 by a predetermined length, is engaged by the separation pawl 134, and the distal end portion of the photosensitive material 22 is peeled from the outer periphery of the heating drum 110. Then, due to reciprocal movement of the separation pawl 134, the pinch roller 136 presses against the photosensitive material 22. Consequently, the photosensitive material 22 is wound round the curve guide roller 132 while being pressed by the pinch roller 136, and moved sideward (of FIG. 1). The photosensitive material 22 that has been wound round the curve guide roller 132 is guided further by the guide plate 138 and the guide roller 144 while being conveyed by the photosensitive material discharge rollers 140, and is accumulated in the waste photosensitive material storage bin 146.

Meanwhile, the image-receiving material 94 from which the photosensitive material has been separated, and which is still in close contact with the heating drum 110, is moved onward to the separation roller 152. When the distal end of the image-receiving material 94 is gripped between the separation roller 152 and the heating drum 110, the separation pawl 154 is moved, also by the cam 116, the distal end of the image-receiving material 94 is engaged by the separation pawl 154, and the image-receiving material 94 is peeled off from the outer periphery of the heating drum 110.

The image-receiving material 94 that has been peeled off from the outer periphery of the heating drum 110 by the separation pawl 154 is further wound around the separation roller 152 and moved downward. The image-receiving material 94 is guided by the guide plate 156 while being conveyed by the image-receiving material discharge rollers 158. Then, the image-receiving material 94 is guided by the image-receiving material guide 160 while being conveyed by the image-receiving material discharge rollers 162 and 164, and discharged to the tray 168.

The image-recording device 10 automatically enters a calibration mode when one or both of the magazines 20 and 92 for the photosensitive material 22 and the image-receiving material 94 is replaced. Even when the image-receiving material has not been replaced, the calibration mode may be initiated by operation of a user.

Figure 16:
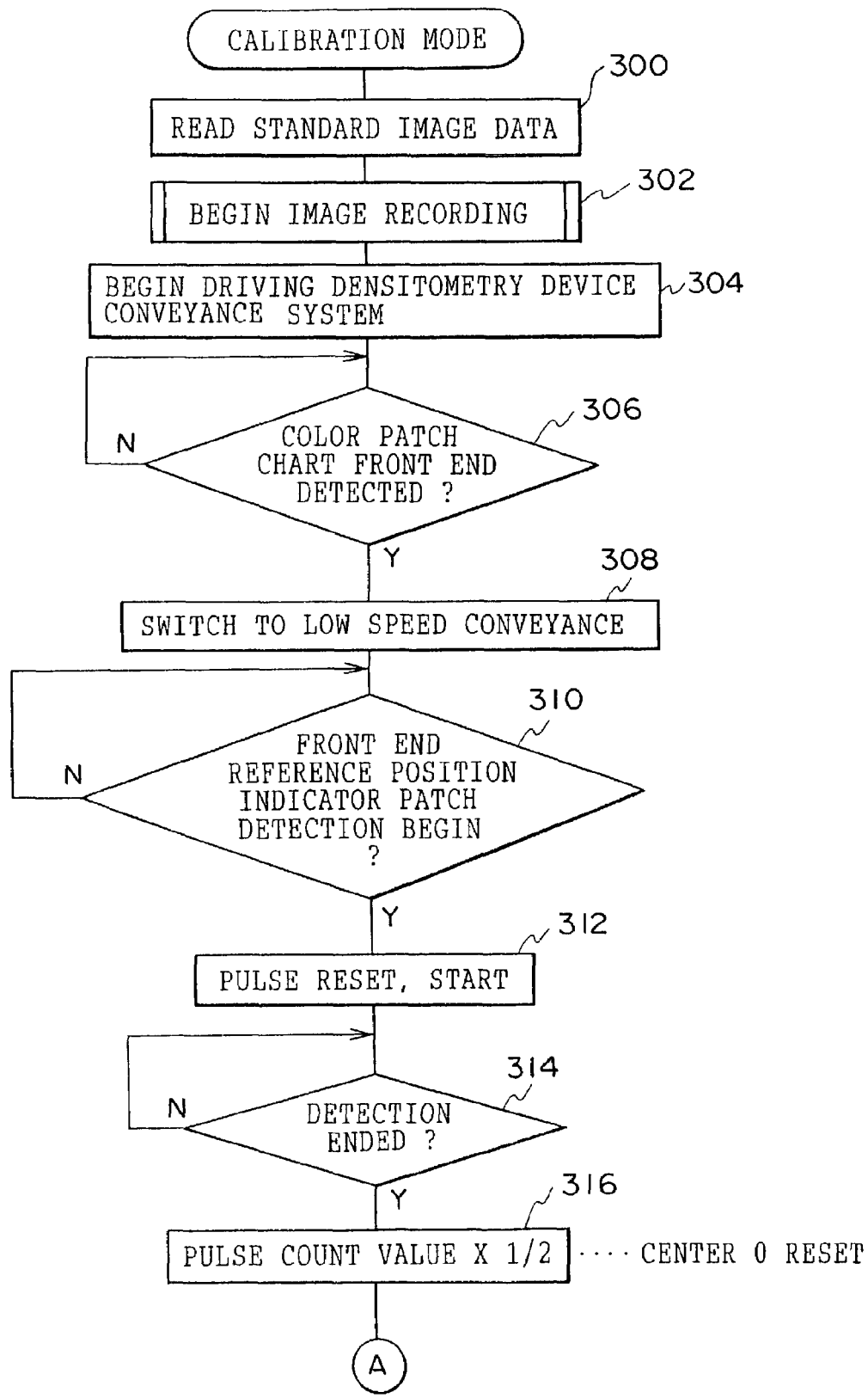
FIG. 16 is a control flow chart showing a first half of a measurement procedure of a densitometry mode.
Figure 17:
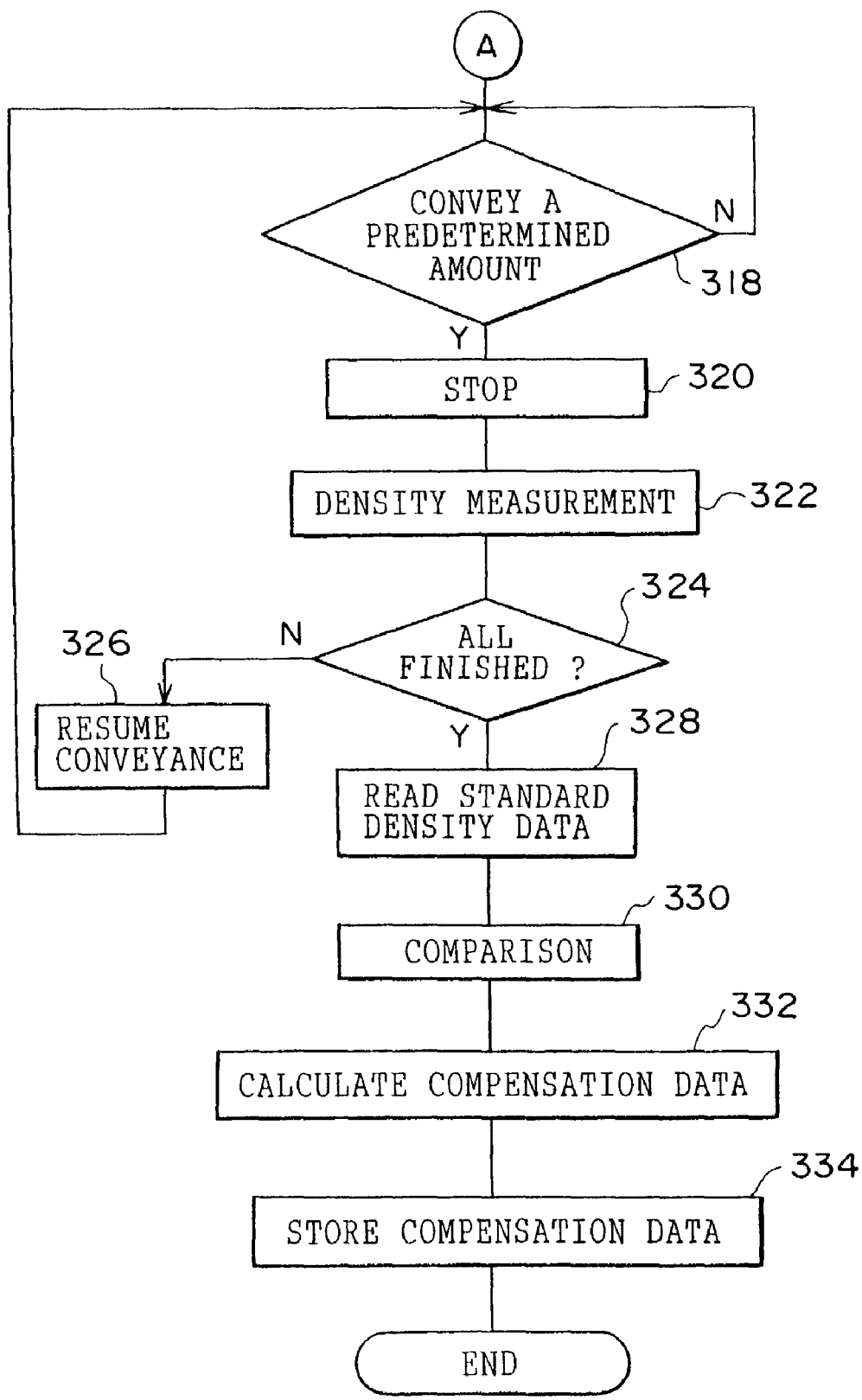
FIG. 17 is a control flow chart showing a latter half of the measurement procedure of the densitometry mode.

Now, the process of the calibration mode will be explained in accordance with the flowchart shown in FIGS. 16 and 17.

In step 300 (see FIG. 16), the standard image data is read. Then, in step 302, the process of recording an image based on the standard image data is begun. This image-recording process is similar to the usual image-recording process described above. Thus, detailed descriptions thereof are not provided here.

In next step 304, driving of the conveyance system of the densitometry device 220 begins. Then, in step 306, it is judged whether or not the front end of the color patch chart 202 has been detected. The color patch chart is manually brought to an insertion end of the densitometry device 220 by the user.

When the color patch chart is inserted at the insertion end of the densitometry device 220, a front end portion of the chart is nipped by the conveyance roller pairs 230. Accordingly, the color patch chart 202 is conveyed at a certain speed by driving force of the conveyance roller pairs 230 (usual conveyance).

When, in step 306, it is judged that the front end of the color patch chart 202 has been detected, control proceeds to step 308. (The front end of the color patch chart 202 is detected when the front end contacts the contact terminal 240 of the limit sensor.) In step 308, conveyance is switched from usual conveyance to slower conveyance.

In step 310, it is judged whether or not the front end edge of the reference position indicator patch 216, which is positioned at the front end side of the color patch chart 202, has been detected. When this judgement is positive, the pulse count, which has been reset to zero, is started in step 312. Then, in step 314, it is judged whether or not the rear end edge of the reference position indicator patch 216 has been detected. When this judgement is positive, in step 316 a position corresponding to half the pulse count value is assigned to a zero reset position.

Thus, a conveyance reference position of the color patch chart 202 is determined. The color patch chart 202 is continuously conveyed for a predetermined number of pulses and then stopped (see steps 318 and 320 in FIG. 17). At the stop position, the center of the first color patch (C1) of the color patch portion 214 substantially coincides with a position of the optical axis of the density measurement optical system according to the photoelectric conversion element 278. Here, density measurement is commenced (step 322).

During conveyance of the color patch chart 202, the actuator 254A of the solenoid 254 is in an extended state, and the pressing plate 242 is in a state of having rotated about the axis 246 so that the pressing portion 244 is submerged with respect to the conveyance support surface of the base portion 224. Therefore, there is no frictional movement between the pressing portion 244 and the color patch chart 202 being conveyed. Because such frictional movement does not occur, the color patch chart 202 is not damaged and resistive forces do not act on the conveyance system.

During density measurement, that is, when the color patch chart 202 is stopped, the actuator 254A of the solenoid 254 is in a withdrawn state. Consequently, the pressing plate 242 is rotated about the axis 246, by the urging force of the compression coil spring 250, in the direction such that the pressing portion 244 pushes up the color patch chart 202. Thus, the color patch chart 202 is precisely protruded to make contact with the protrusion-contact portion 274 of the housing 260. Therefore, a focusing depth is not deviated from.

When the density measurement in step 322 has finished, in step 324 it is judged whether or not all density measurements have been completed for the color patches on the color patch chart 202. If this judgement is negative, conveyance is resumed in step 326, control returns to step 318, and the above-described steps are repeated for each of the color patches.

When this judgement is positive, that is, when density measurement has been completed for all the color patches, control proceeds to step 328 and the standard density data is read out.

In step 330, density measurement data is compared with the standard density data. Then, in step 332, compensation data is calculated. In step 334, the calculated compensation data is stored. This is the final step of this routine.

Accordingly, during subsequent processes for recording usual images, data signals that are read are modified in accordance with the compensation data. Thus, differences in density and tone between lot units of the photosensitive material 22 and the image-receiving material 94 can be compensated for.

Each time the above-described densitometry is performed or at regular intervals, it is necessary to set white balance of the photoelectric conversion element 278. Conventionally, an operation such as insertion of a blank sheet of paper into the densitometry device 220 would have been performed. However, in the present embodiment, the white plate 256 is provided at the pressing surface of the pressing portion 244. Therefore, the white plate 256 can be positioned on the optical axis of the density measurement optical system, without anything needing to be inserted into the densitometry device 220. Thus, operability is markedly improved.

Moreover, in the present embodiment, the housing 260 that holds the density measurement optical system is moveable along the shaft 264, and is linked to the closing cover 270 provided at the cover 226, for opening and closing the closing cover 270. Thus, by opening this closing cover 270, the housing 260 is opened up, and an operation space for wiping the plate 256 can be assured. In other words, when the closing cover 270 has opened, a cotton swab or the like can be inserted through an aperture portion 268 that has opened and the white plate 256 can easily be cleaned.

In the present embodiment, chips of each of red, green and blue are built into the cannon shell-like LED chip 282. The color patch chart 202, which is protruded to make contact with the protrusion-contact portion 274, is illuminated by light of each color in turn.

The LED chip 282 is held by the holding plate 284 of the housing 260 such that the chips of the respective colors are arranged in a single row along the conveyance direction of the color patch chart 202, and the optical axis of the LED chip 282 forms an angle $\theta$ with the optical axis of the density measurement optical system of 52°.

The shell-shaped light emitting portion of the LED chip 282 is inserted into the round hole 286 formed in the holding plate 284. Because the base plate 282C at the base portion side of the LED chip 282 fits with the periphery of the round hole 286, the LED chip 282 can be positioned. In this positioned state, the restraining plate 288 pushes against the base portion 282C, due to the urging caused by the intrinsic plate spring functionality of the restraining plate 288. Thus, the LED chip 282 is held by the holding plate 284. The restraining plate 288 is provided with the slit-form cutaway portion for preventing interference with the four terminals 282D, 282E, 282F and 282H. Also, one end portion of the restraining plate 288 is engaged with the connecting portion that connects the housing 260 to the holding plate 284, and the other end of the restraining plate 288 is screwed to the holding plate 284 by the screws 292.

A permissible range for the angle $\theta$ is 47° to 55°. By maintaining the angle thus, a sufficient light amount for measuring density is provided when the single LED chip 282 is caused to illuminate by a predetermined voltage (this is the reason for the lower limit of 47°), and direct incidence on the photoelectric conversion element 278 of light that has been reflected at the surface of the color patch chart 202 is avoided (this is the reason for the upper limit of 55°).

The four terminals 282D, 282E, 282F and 282H protrude through the base plate 282C at the base portion of the shell-shaped light emitting portion of the LED chip 282. Usually, attachment holes would be formed in advance in a base plate, and these terminals would essentially be inserted through these holes and soldered. However, in the present embodiment, the leads 290 are directly connected to the terminals. In order to prevent members that connect the terminals 282D, 282E, 282F and 282H with the leads 290 from encountering and making contact with one another (a short-circuit), connection portions of the terminals 282D, 282E, 282F and 282H that connect with the leads 290 are covered by the insulation tubes 294.

Because the terminals 282D, 282E, 282F and 282H are shielded by the insulation tubes 294, the terminals are curved so as to be splayed apart along the direction in which the terminals are lined up. Consequently, even if the basic pitch between the terminals is smaller than the outer diameters of the insulation tubes 294, the insulation tubes 294 can be applied with certainty.

The present embodiment has been described for a case in which the present invention is applied to an exposure device that uses a photosensitive material. However, the present invention may also be applied to electrophotographic devices, ink jet printers, thermal printers, and other types of image-forming devices.

A densitometry device relating to the present invention as described above can perform suitable densitometry with minimum required light amounts and can achieve space savings.

Also, because the light source, which requires only space for a single light source and does not require greater space, emits light in respective colors, color filters do not have to be provided.

What is claimed is:

1. A densitometry device for measuring densities of an object of measurement on which a color image is formed that includes a pattern of different densities for each of colors, the device comprising:
    an LED light source that includes an individual package and a plurality of light-emitting chips enclosed in the package for illuminating light of at least two colors onto the object of measurement; and
    a density measurement optical system that photoelectrically converts light that has been at least one of reflected from and transmitted through the object of measurement for obtaining electric signals, such that densities of each of the density patterns are obtained from the electric signals.

2. The densitometry device according to claim 1, further comprising a plurality of power supply terminals for enabling the light-emitting chips to emit light, the terminals each including a connection portion which connects to a corresponding lead and is shielded by an insulating member, the terminals being bent at predetermined positions such that positions to be shielded are maintained substantially in a state of non-contact with respect to one another.

3. The densitometry device according to claim 1, further comprising a housing which accommodates the LED light source and the density measurement optical system, the housing being formed with electrically conductive members.

4. A densitometry device comprising:
    a light source for illuminating an object of measurement on which an image is formed that includes a pattern of different densities; and
    a density measurement optical system that photoelectrically converts light that has been at least one of reflected from and transmitted through the object of measurement, for obtaining densities of the pattern of densities;
    wherein an optical axis of the light source and an optical axis of the density measurement optical system are set such that, during illumination of the object of measurement, the optical axes form an angle in the range from 47 to 55; and
    wherein the pattern of densities of the object of measurement includes an arrangement direction, and the light source includes a plurality of light-emitting chips arranged along a single straight row, a direction of arrangement of the light-emitting chips substantially coinciding with the arrangement direction of the density pattern.

5. The densitometry device according to claim 4, wherein each of the light-emitting chips is capable of emitting light of a color, and the colors that can be emitted by the light-emitting chips are different from one another.

6. The densitometry device according to claim 5, further comprising a plurality of power supply terminals for enabling the light-emitting chips to emit light, each of the terminals including a distal end portion for connecting to a corresponding lead and being shielded by an insulating member, and a proximal end portion which is bent such that positions to be shielded are maintained substantially in a state of non-contact with respect to one another.

7. The densitometry device according to claim 6, wherein the terminals are arranged along an arrangement direction, and directions in which the terminals are bent coincide with the arrangement direction of the terminals.

8. The densitometry device according to claim 6, further comprising a holding member with a pre-specified angle of inclination, and a gripping member through which the power supply terminals of the light source pass, the holding member and the gripping member resiliently supporting the light source, and the gripping member including a cutaway portion for avoiding contact thereof with the power supply terminals of the light source.

9. The densitometry device according to claim 4, further comprising a housing for holding the light source and the density measurement optical system, the housing being formed with electrically conductive members.

10. The densitometry device according to claim 1, wherein conveyance direction lengths of the density patterns increase along a conveyance direction.

11. The densitometry device according to claim 3, wherein the housing comprises a conductive synthetic resin.

12. The densitometry device according to claim 1, wherein each of the plurality of light-emitting chips emit light substantially along an optical axis.

* * * * *